(12) United States Patent  (10) Patent No.: US 10,695,427 B2
Guo et al.                  (45) Date of Patent:    Jun. 30, 2020

(54) SHAPE MEMORY PARTICLES FOR BIOMEDICAL USES

(71) Applicant: The Johns Hopkins University, Baltimore, MD (US)

(72) Inventors: Qiongyu Guo, College Park, MD (US); Jordan J. Green, Nottingham, MD (US); Randall A. Meyer, Baltimore, MD (US); Corey J. Bishop, Arlington, MA (US); Anand Kumar, Baltimore, MD (US); Gregg L. Semenza, Reisterstown, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/564,461

(22) PCT Filed: Apr. 6, 2016

(86) PCT No.: PCT/US2016/026209
§ 371 (c)(1),
(2) Date: Dec. 14, 2017

(87) PCT Pub. No.: WO2016/164458
PCT Pub. Date: Oct. 13, 2016

(65) Prior Publication Data
US 2018/0140702 A1    May 24, 2018

Related U.S. Application Data

(60) Provisional application No. 62/257,278, filed on Nov. 19, 2015, provisional application No. 62/143,482, filed on Apr. 6, 2015.

(51) Int. Cl.
*A61K 41/00* (2020.01)
*A61K 47/69* (2017.01)
(Continued)

(52) U.S. Cl.
CPC ........ *A61K 41/0028* (2013.01); *A61K 9/1647* (2013.01); *A61K 31/473* (2013.01);
(Continued)

(58) Field of Classification Search
CPC ............ A61K 41/0028; A61K 31/7048; A61K 31/473; A61K 45/06; A61K 47/6925;
(Continued)

(56) References Cited

U.S. PATENT DOCUMENTS

2007/0099952 A1   5/2007  Van Meir et al.
2009/0324552 A1*  12/2009 Lichter ............... A61K 9/0046
                                                        424/93.4
(Continued)

FOREIGN PATENT DOCUMENTS

WO    2007084418 A2    7/2007
WO    2007097605 A1    8/2007
(Continued)

OTHER PUBLICATIONS

Zhang, Honghi et al, "Optically Triggered and Spatially Controllable Shaped-Memory Polymer Gold Nanoparticle Composite Materials", Journal of Materials Chemical, 2012, vol. 22, pp. 845-849.*
(Continued)

*Primary Examiner* — Carlos A Azpuru
(74) *Attorney, Agent, or Firm* — Casimir Jones, S.C.; Jeffrey W. Childers

(57) ABSTRACT

The presently disclosed subject matter provides compositions, methods, and kits comprising shape memory particles that can be used for delivering a drug and/or treating a disease or disorder in a patient. Specifically, shape changes in the presently disclosed shape memory particles can be used to control drug delivery spatially and/or temporally in a patient. Also provided are compositions, methods, and kits comprising nanoparticles and hypoxia-inducible factor
(Continued)

POLYMER CHAIN

GOLD NANOPARTICLES

POLYMER ENTANGLEMENT AS PHYSICAL CROSSLINKS (HIF) inhibitors with or without chemotherapeutic agents for inhibiting HIF activity in a patient and/or treating a hypoxia-associated disease or disorder.

10 Claims, 23 Drawing Sheets

(51) Int. Cl.
*C07K 16/00* (2006.01)
*A61K 9/16* (2006.01)
*A61P 35/04* (2006.01)
*A61P 35/00* (2006.01)
*A61K 31/473* (2006.01)
*A61K 31/7048* (2006.01)
*A61K 45/06* (2006.01)
*B82Y 5/00* (2011.01)

(52) U.S. Cl.
CPC .......... *A61K 31/7048* (2013.01); *A61K 45/06* (2013.01); *A61K 47/6925* (2017.08); *A61K 47/6937* (2017.08); *A61P 35/00* (2018.01); *A61P 35/04* (2018.01); *C07K 16/00* (2013.01); *B82Y 5/00* (2013.01)

(58) Field of Classification Search
CPC .. A61K 47/6937; A61K 9/1647; A61K 35/04; A61P 35/00
See application file for complete search history.

(56) References Cited

U.S. PATENT DOCUMENTS

2013/0274217 A1* 10/2013 Hanes ................. A61K 9/0048
514/34
2014/0147510 A1 5/2014 Lahann et al.
2014/0186679 A1 7/2014 Archer et al.

FOREIGN PATENT DOCUMENTS

| WO | 2010132879 A2 | 11/2010 |
| WO | 2013152314 A1 | 10/2013 |
| WO | 2014138085 A1 | 9/2014 |
| WO | 2014143871 A2 | 9/2014 |

OTHER PUBLICATIONS

Zhang et al, Optically Triggered and Spatially Controllable Shape-Memory Polymer Gold Nanoparticle, Journal of Material Chenistry , 2012, vol. 22, pp. 845-849. (Year: 2012).*
Zhang, Hongji et al. "Optically Triggered and Spatially Controllable Shape-Memory Polymer-Gold Nanoparticle Composite Materials." Journal of Materials Chemistry, 2012, vol. 22, pp. 845-849.
International Search Report issued in PCT/US2016/026209 dated Jun. 13, 2016.
Chaterjee et al., Synthesis and Self-assembly of DMPC-conjugated Gold Nanoparticles. Mater. Res. Soc. Symp. Proc. 2008;1061 7 pages https://doi.org/10.1557/PROC-1061-MM09-08.
Liu et al., Extinction coefficient of gold nanoparticles with different sizes and different capping ligands. Colloids and Surfaces B: Biointerfaces 2007;58:3-7.
Meyer et al., An automated multidimensional thin film stretching device for the generation of anisotropic polymeric micro- and nanoparticles. J Biomed Mater Res A. Aug. 2015;103(8):2747-57.
Luo, et al., An indicator-guided photo-controlled drug delivery system based on mesoporous silica/gold nanocomposites. Nano Research. Jun. 2015;8(6):1893-1905.
Chapman, PEGylated antibodies and antibody fragments for improved therapy: a review. Adv Drug Deliv Rev. Jun. 17, 2002;54(4):531-45.
Cunningham-Rundles, et al., Biological activities of polyethylene-glycol immunoglobulin conjugates. Resistance to enzymatic degradation. J Immunol Methods. Aug. 10, 1992;152(2):177-90.
Kull, et al., Mixtures of Quaternary Ammonium Compounds and Long-chain Fatty Acids as Antifungal Agents. Appl Microbiol. Nov. 1961;9(6):538-541.
Le, et al., Near-infrared activation of semi-crystalline shape memory polymer nanocomposites. J Applied Polymer Science. Dec. 2013;130(6):4551-4557.
Xiao, et al., Shape matters: A gold nanoparticle enabled shape memory polymer triggered by laser irradiation. Particle and Particle Systems Characterization. Apr. 2013;30(4):338-345.
Guo, et al., Tailored drug release from biodegradable stent coatings based on hybrid polyurethanes. J Control Release. Aug. 4, 2009;137(3):224-33.
Meyer, et al., Biodegradable nanoellipsoidal artificial antigen presenting cells for antigen specific T-cell activation. Small. Apr. 2015;11(13):1519-25.
Zhang, et al., Polymers with dual light-triggered functions of shape memory and healing using gold nanoparticles. ACS Appl Mater Interfaces. Dec. 26, 2013;5(24):13069-75.

* cited by examiner

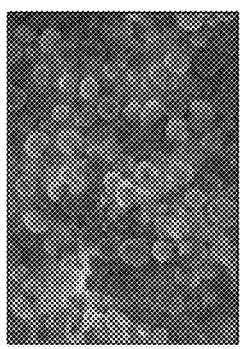
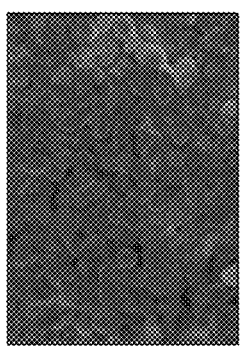
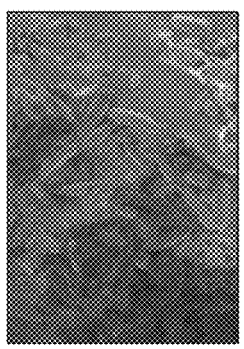
FIG. 5A
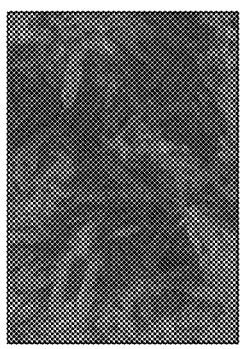
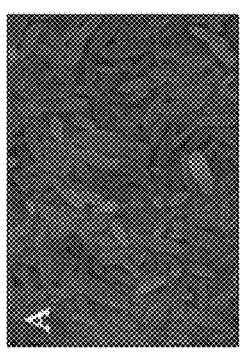
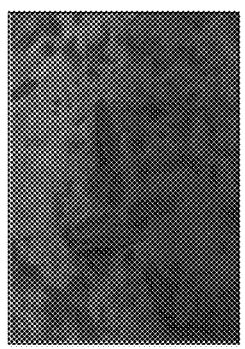
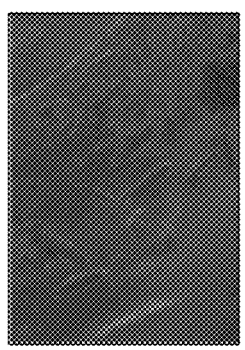
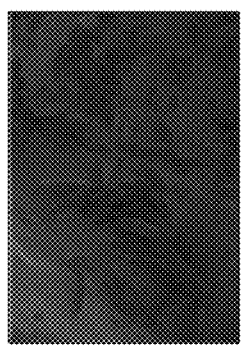
FIG. 5B
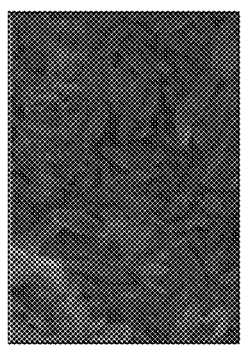
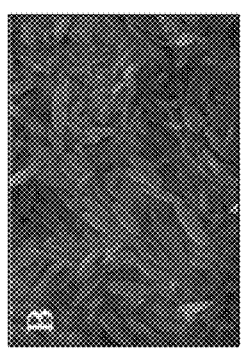

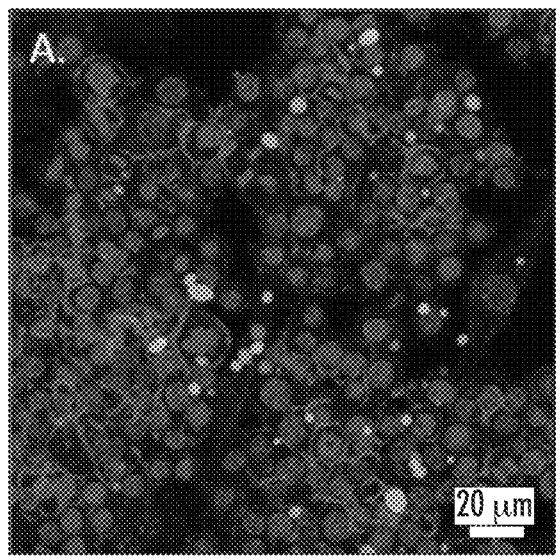
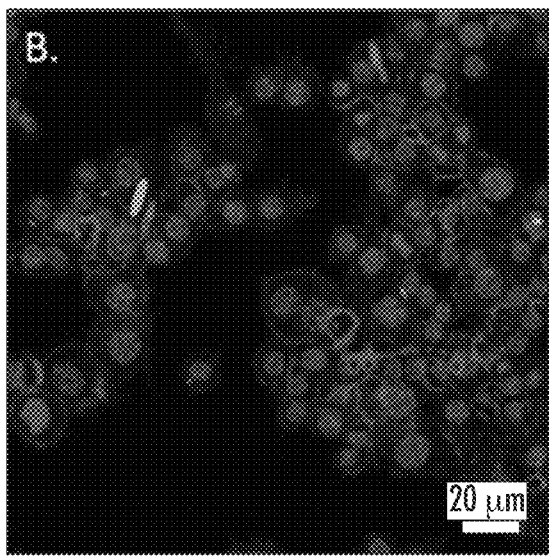
FIG. 7A  FIG. 7B
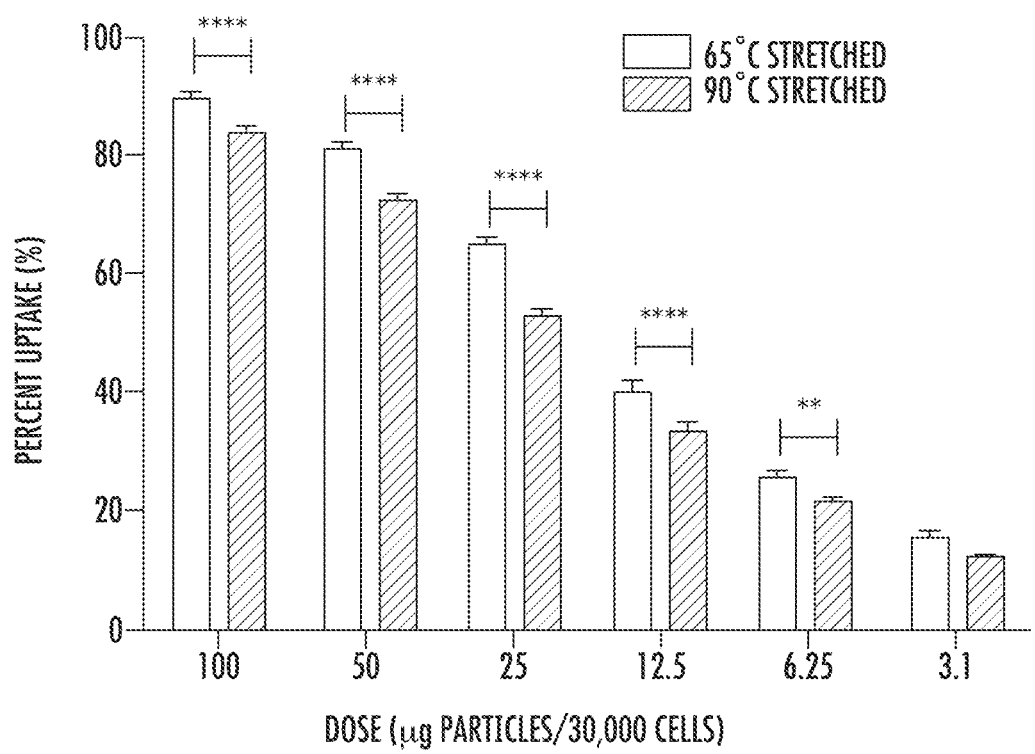
FIG. 7C

SHAPE MEMORY PARTICLES FOR BIOMEDICAL USES

CROSS-REFERENCE TO RELATED APPLICATIONS

This application claims the benefit of U.S. Provisional Application Nos. 62/143,482, filed Apr. 6, 2015, and 62/257,278, filed Nov. 19, 2015, the contents of which are incorporated herein by reference in their entirety.

FEDERALLY SPONSORED RESEARCH OR DEVELOPMENT

This invention was made with government support under R01-EB016721 awarded by the National Institutes of Health (NIH). The government has certain rights in the invention.

BACKGROUND

Shape memory effect is an unconventional mechanical functionality that is enabling for many biomedical applications. Shape memory polymers are unique in that they are "smart" and can undergo shape-transformations upon triggering by different external stimuli such as heat, light and electricity. However, the lack of biocompatibility of either triggering environment or shape memory polymers themselves has been a main issue preventing these polymers from biomedical applications.

Drug carrier systems hold great potential to modify pharmacokinetics and safety profiles in cancer chemotherapy, but specific formulations that are safe and effective for the delivery of one or more hypoxia-inducible factor (HIF) inhibitors are not known to the field. For example, dose-limiting toxicity in humans does not allow digoxin to be used as an effective anti-cancer agent.

SUMMARY

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning. A Laboratory Manual*, $3^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange $10^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact.shtml.

All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

In some aspects, the presently disclosed subject matter provides a composition comprising an anisotropic shape memory particle comprising a polymeric matrix and at least one stimuli-sensitive nanoparticle.

In some aspects, the presently disclosed subject matter provides a method for delivering a drug to a patient, the method comprising: (a) administering to a patient an anisotropic shape memory particle comprising a polymeric matrix and at least one stimuli-sensitive nanoparticle, wherein the anisotropic shape memory particle is loaded with at least one drug; and (b) stimulating the at least one stimuli-sensitive nanoparticle to release the at least one drug from the anisotropic shape memory particle at a target location inside the patient.

In some aspects, the presently disclosed subject matter provides a method for treating a disease or disorder in a patient in need thereof, the method comprising: (a) administering to a patient an anisotropic shape memory particle comprising a polymeric matrix and at least one stimuli-sensitive nanoparticle, wherein the anisotropic shape memory particle is loaded with at least one drug that is capable of treating a disease or disorder; and (b) stimulating the at least one stimuli-sensitive nanoparticle to release the at least one drug from the anisotropic shape memory particle at a target location inside the patient, thereby treating the disease or disorder in the patient.

In some aspects, the presently disclosed subject matter provides a composition comprising a nanoparticle comprising a polymeric matrix and at least one hypoxia-inducible factor (HIF) inhibitor.

In some aspects, the presently disclosed subject matter provides a method for inhibiting one or more hypoxia-inducible factors (HIFs) in a patient, the method comprising administering to a patient an anisotropic nanoparticle that is loaded with at least one HIF inhibitor, thereby inhibiting the one or more HIF in the patient.

In some aspects, the presently disclosed subject matter provides a method for treating a hypoxia-associated disease or disorder in a patient in need thereof, the method comprising administering to a patient an anisotropic nanoparticle that is loaded with at least one HIF inhibitor, thereby treating the hypoxia-associated disease or disorder in the patient.

In some aspects, the presently disclosed subject matter provides a method for inhibiting one or more hypoxia-inducible factors (HIFs) in a patient, the method comprising administering to a patient a nanoparticle comprising a polymeric matrix, wherein the nanoparticle is loaded with at least one HIF inhibitor, thereby inhibiting the one or more HIFs in the patient.

In some aspects, the presently disclosed subject matter provides a method for treating a hypoxia-associated disease or disorder in a patient in need thereof, the method comprising administering to a patient a nanoparticle comprising a polymeric matrix, wherein the nanoparticle is loaded with at least one HIF inhibitor, thereby treating the hypoxia-associated disease or disorder in the patient.

In some aspects, the presently disclosed subject matter provides a kit comprising a composition comprising an anisotropic shape memory particle comprising a polymeric matrix and at least one stimuli-sensitive nanoparticle.

In some aspects, the presently disclosed subject matter provides a kit comprising a composition comprising a nanoparticle comprising a polymeric matrix and at least one hypoxia-inducible factor (HIF) inhibitor.

In some embodiments, the nanoparticle comprising a polymeric matrix and at least one HIF inhibitor is anisotropic. In some embodiments, the nanoparticle or the anisotropic nanoparticle comprising a polymeric matrix and at least one HIF inhibitor further comprises at least one stimuli-sensitive nanoparticle. In some embodiments, the method further comprises stimulating the at least one stimuli-sensitive nanoparticle in order to release the HIF inhibitor in a target location inside the patient.

In some embodiments, the presently disclosed subject matter further comprises targeting the anisotropic shape memory particle, the nanoparticle, or the anisotropic nanoparticle to a target location inside the patient. In some embodiments, the target location is a cancer site. In some embodiments, the target location is a solid tumor and/or a metastatic site.

In some embodiments, the surface of the anisotropic shape memory particle, the nanoparticle, or the anisotropic nanoparticle comprises at least one biomolecule. In some embodiments, at least one biomolecule comprises a targeting agent and/or therapeutic agent. In some embodiments, the targeting agent and/or therapeutic agent is selected from the group consisting of a small molecule, carbohydrate, sugar, protein, peptide, nucleic acid, antibody or antibody fragment thereof, hormone, hormone receptor, receptor ligand, and cancer cell specific ligand. In some embodiments, at least one biomolecule comprises an antibody.

In some embodiments, the anisotropic shape memory particle, the nanoparticle, or the anisotropic nanoparticle is biodegradable and/or biocompatible in the patient. In some embodiments, the polymeric matrix is poly(lactic acid)-based. In some embodiments, the poly(lactic acid)-based polymeric matrix comprises poly(D,L-lactide-co-glycolide) (PLGA) or poly (D,L-lactic acid) (PDLLA).

In some embodiments, the anisotropic shape memory particle ranges in size from about 10 nanometers to about 500 microns. In some embodiments, the nanoparticle or the anisotropic nanoparticle comprising at least one HIF inhibitor, or the nanoparticle or the anisotropic nanoparticle comprising a polymeric matrix and at least one HIF inhibitor ranges in size from about 10 nanometers to about 500 microns.

In some embodiments, the polymeric matrix is stretched at a temperature from above the polymer transition temperature up to the polymer degradation temperature to form an anisotropic polymeric matrix. In some embodiments, the polymeric matrix is stretched at a temperature above but close to the polymer transition temperature. In some embodiments, stretching of the polymeric matrix causes the polymeric matrix to change from a generally spherical shape to an anisotropic shape.

In some embodiments, at least one stimuli-sensitive nanoparticle comprises gold and/or iron. In some embodiments, at least one stimuli-sensitive nanoparticle can be spatially and/or temporally activated. In some embodiments, stimulating at least one stimuli-sensitive nanoparticle occurs by stimulating the patient. In some embodiments, at least one stimuli-sensitive nanoparticle is activated by or the patient is stimulated by at least one stimulus selected from the group consisting of heat, light, and electricity. In some embodiments, the activation of at least one stimuli-sensitive nanoparticle or the stimulation of the patient induces the shape of the anisotropic shape memory particle or the anisotropic nanoparticle to change. In some embodiments, activation of at least one stimuli-sensitive nanoparticle or the stimulation of the patient induces the shape of the anisotropic shape memory particle or the anisotropic nanoparticle to change from an anisotropic shape to another anisotropic shape or a generally spherical shape. In some embodiments, the change in shape of the anisotropic shape memory particle or the anisotropic nanoparticle simultaneously happens with the release of at least one drug molecule from the anisotropic shape memory particle or the anisotropic nanoparticle. In some embodiments, the release of at least one drug molecule occurs in a range from about 1 day to about two months after the anisotropic shape memory particle or the anisotropic nanoparticle changes shape. In some embodiments, the change in shape of the anisotropic shape memory particle or the anisotropic nanoparticle occurs in a patient.

In some embodiments, the stimulus is applied external to the patient in proximity to a target location inside the patient. In some embodiments, the target location of the patient comprises a solid tumor and/or a metastatic site. In some embodiments, the anisotropic shape memory particle or the anisotropic nanoparticle is not taken up by a macrophage in the patient.

In some embodiments, the hypoxia-associated disease or disorder is cancer or an ocular disease. In some embodiments, the cancer is selected from the group consisting of brain, colon, breast, prostate, liver, kidney, lung, esophagus, head and neck, ovarian, cervical, stomach, colon, rectal, bladder, uterine, testicular, and pancreatic. In some embodiments, the ocular disease is selected from the group consisting of diabetic retinopathy, macular degeneration, and macular edema. In some embodiments, the hypoxia-associated disease or disorder is chemotherapy resistance.

In some embodiments, at least one drug is an HIF inhibitor. In some embodiments, the HIF inhibitor is a cardiac glycoside, an anthracycline, or an HIF-1 dimerization inhibitor. In some embodiments, the HIF inhibitor is digoxin or acriflavine.

In some embodiments, the presently disclosed methods further comprise administering a chemotherapeutic agent along with the HIF inhibitor. In some embodiments, the presently disclosed composition or kit further comprises a chemotherapeutic agent. In some embodiments, the chemotherapeutic agent is paclitaxel or gemcitabine.

In some embodiments, the HIF is selected from the group consisting of hypoxia-inducible factor-1 (HIF-1), hypoxia-inducible factor-2 (HIF-2), and hypoxia-inducible factor-3 (HIF-3).

In some embodiments, the presently disclosed subject matter provides for the use of a presently disclosed composition for the treatment of a disease or disorder. In some embodiments, the presently disclosed subject matter provides for the use of a presently disclosed composition for the manufacture of a medicament for the treatment of a disease or disorder.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
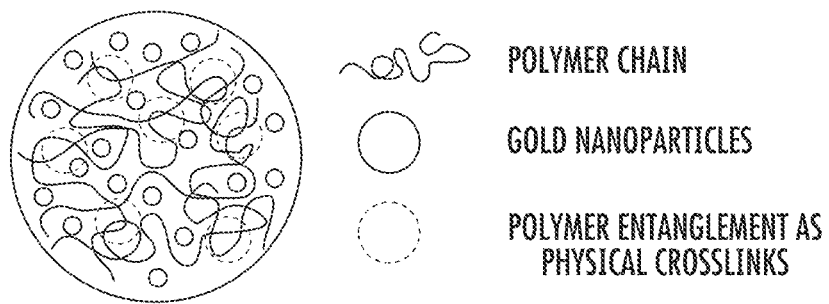
Figure 1B:
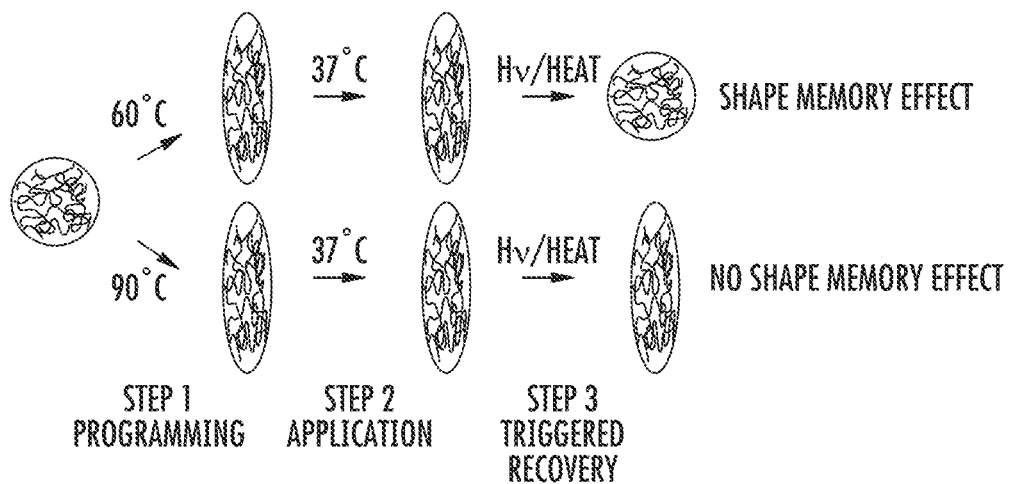
Figure 2A:
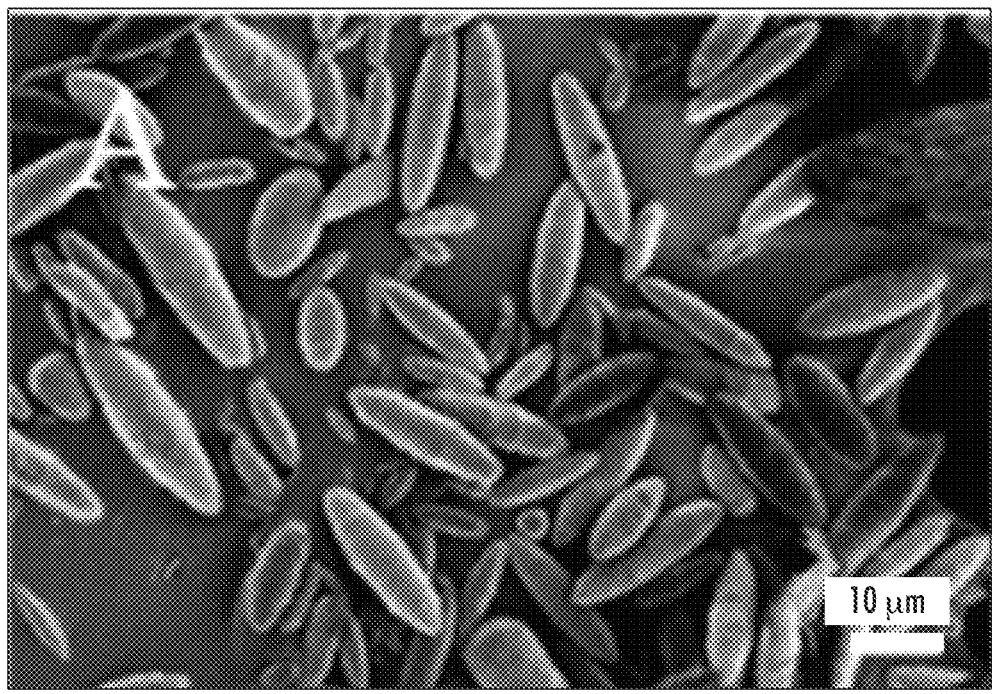
Figure 2B:
Figure 2C:
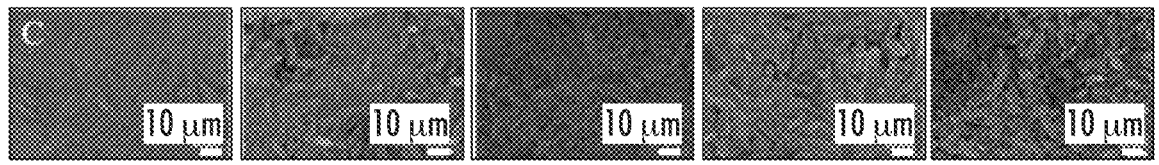
Figure 2D:
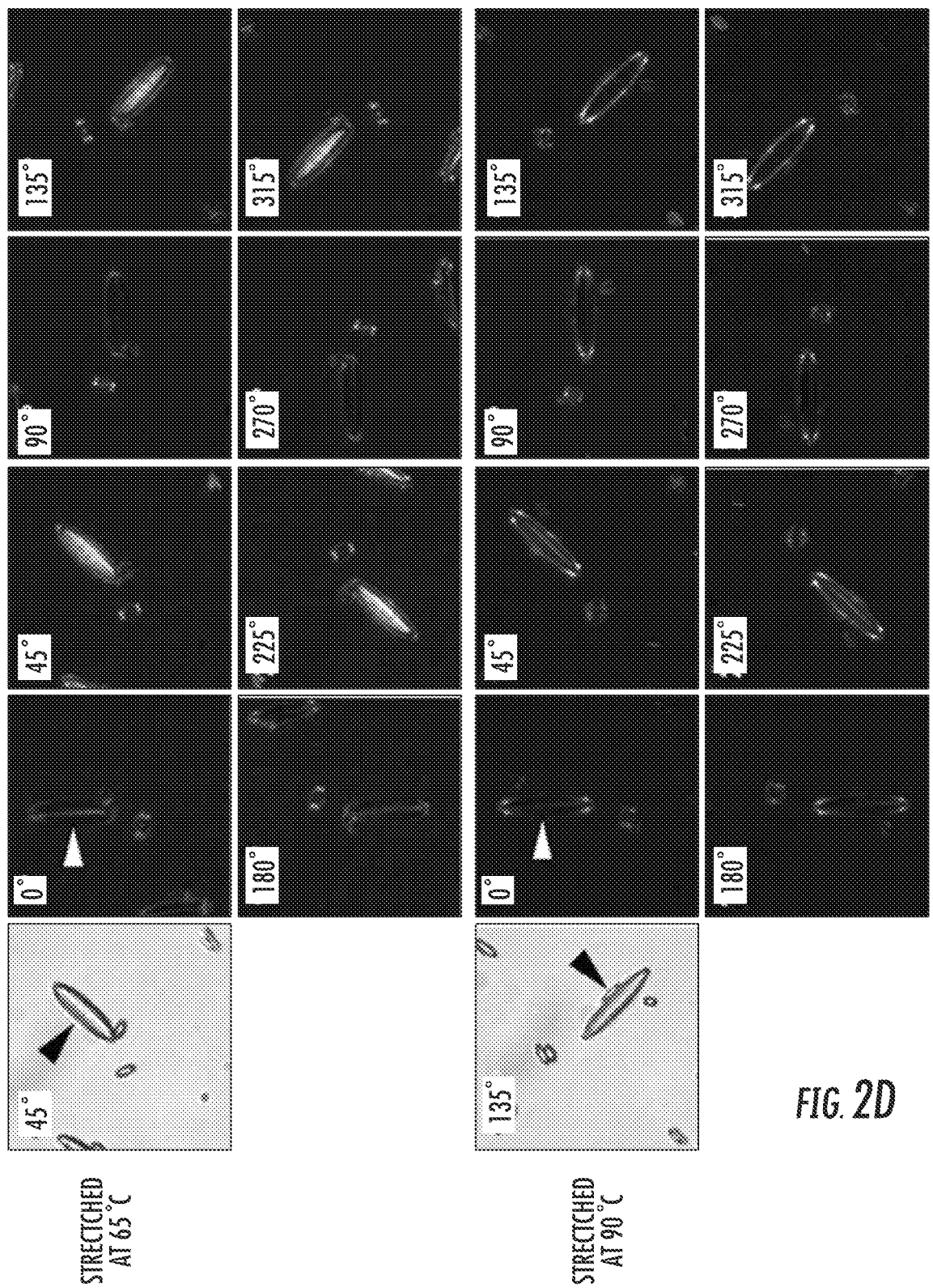
Figure 3A:
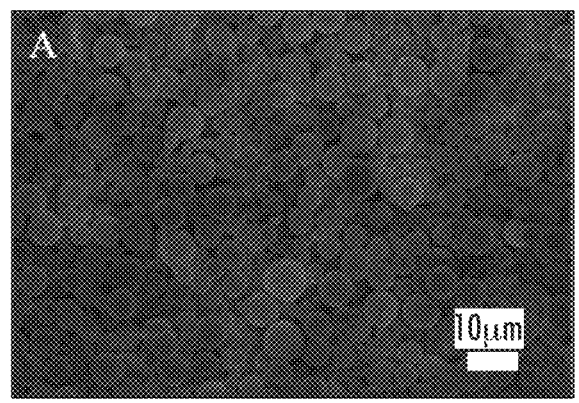
Figure 3B:
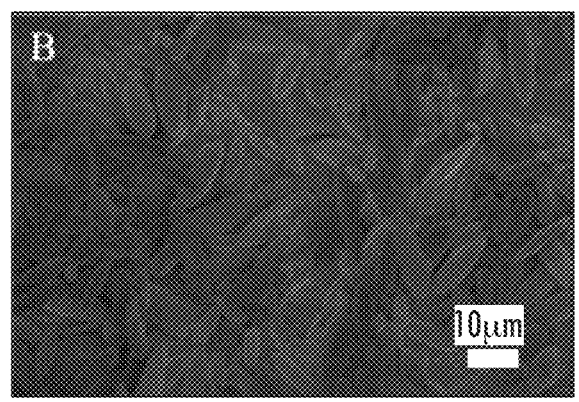
Figure 3C:
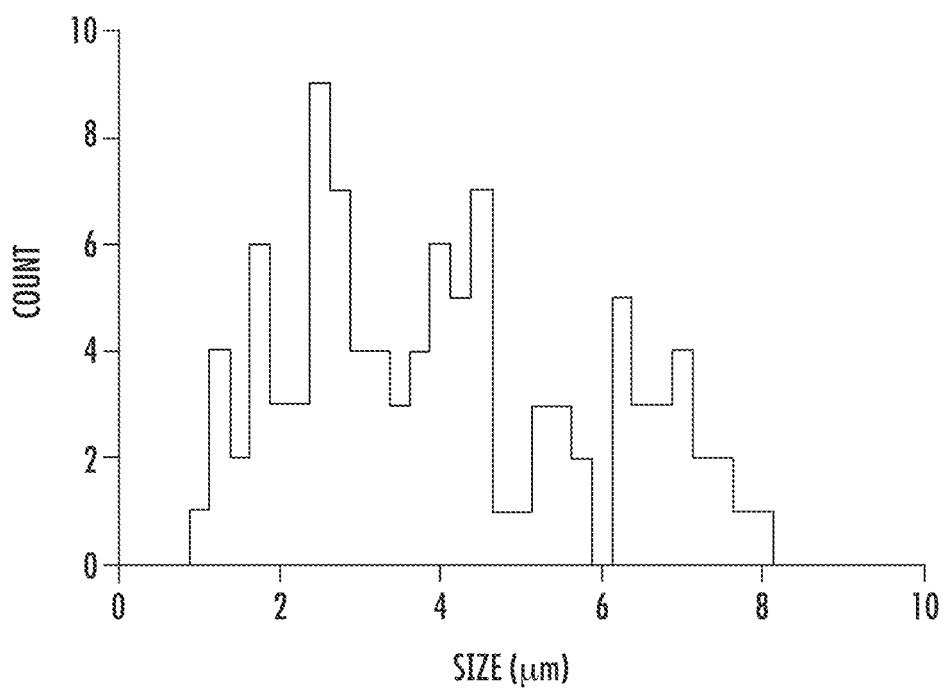
Figure 3D:
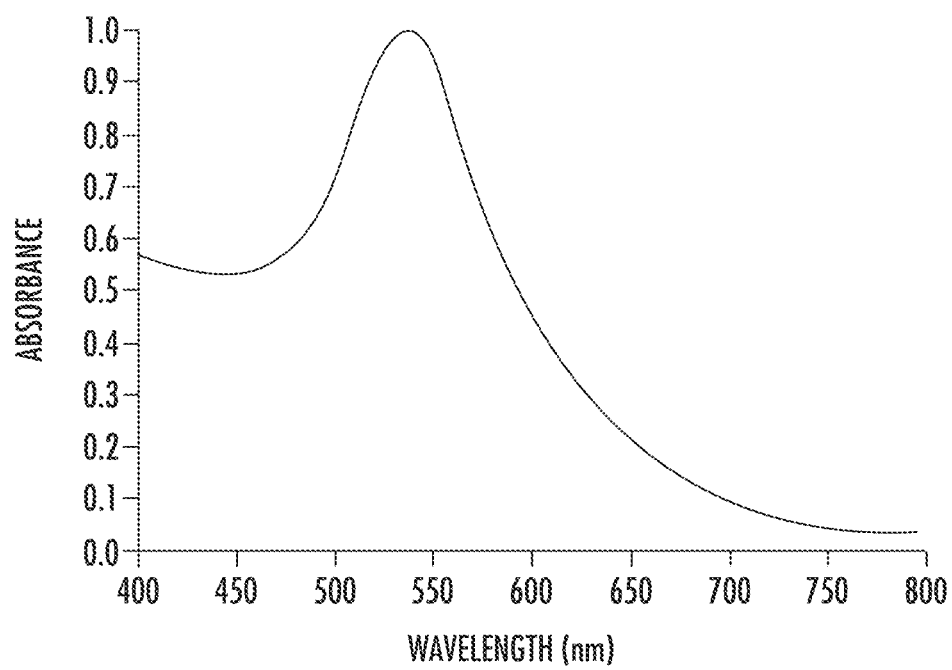
Figure 3E:
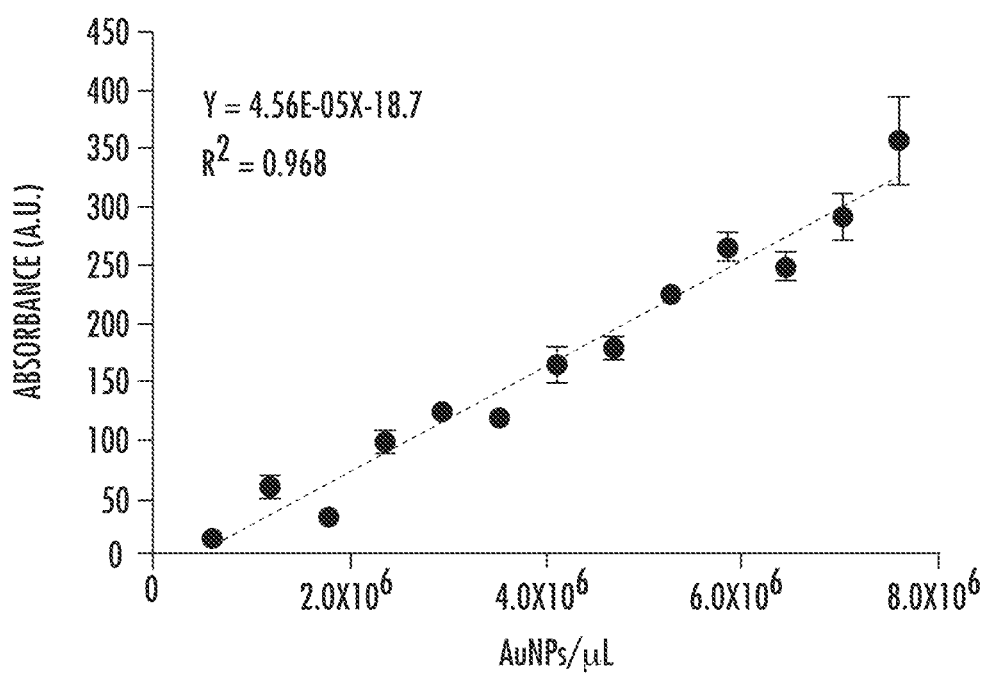
Figure 5C:
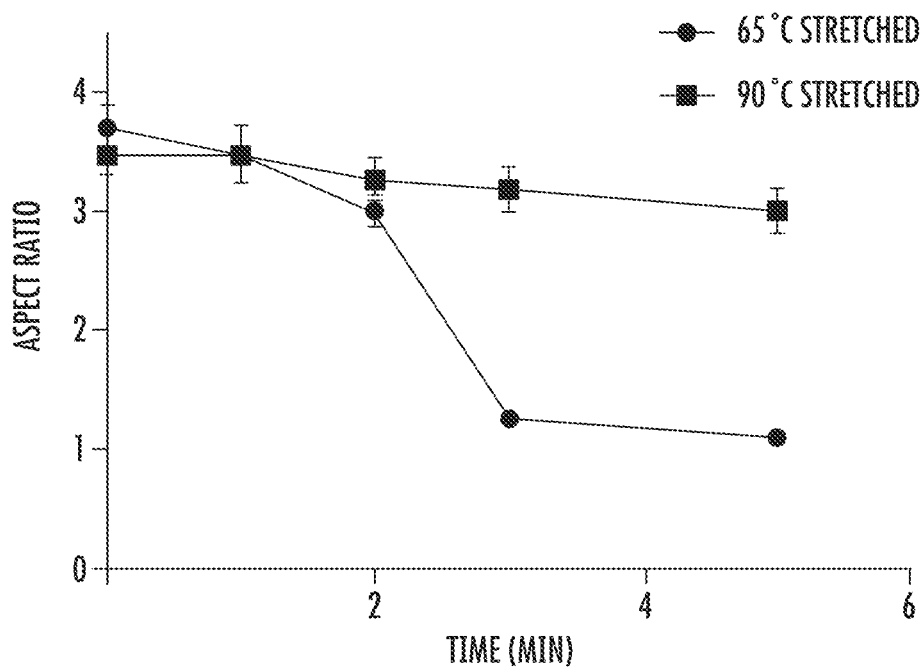
Figure 5D:
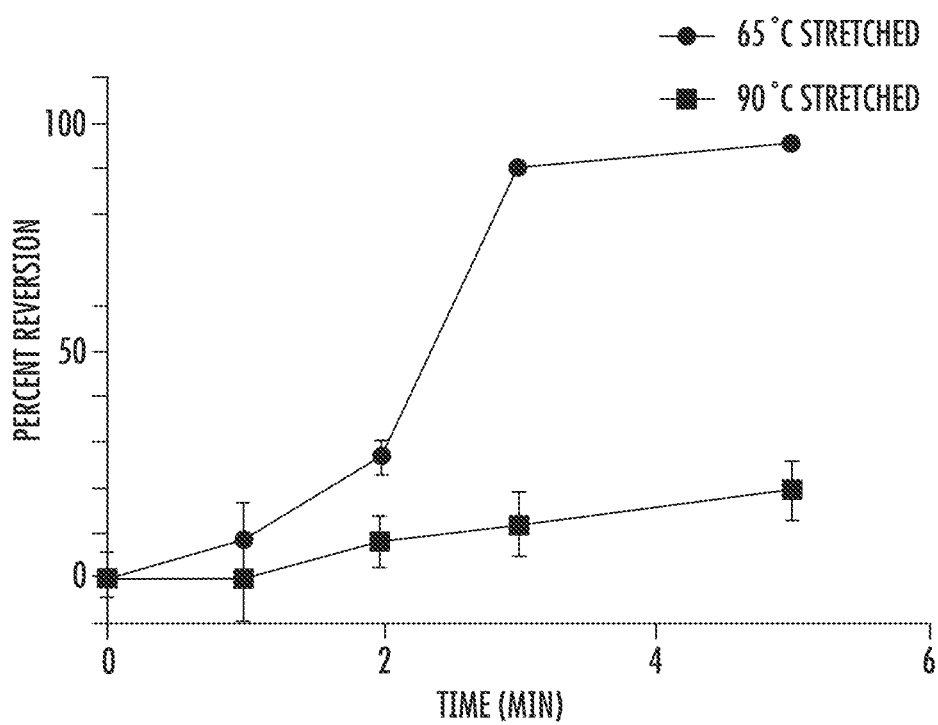
Figure 5E:
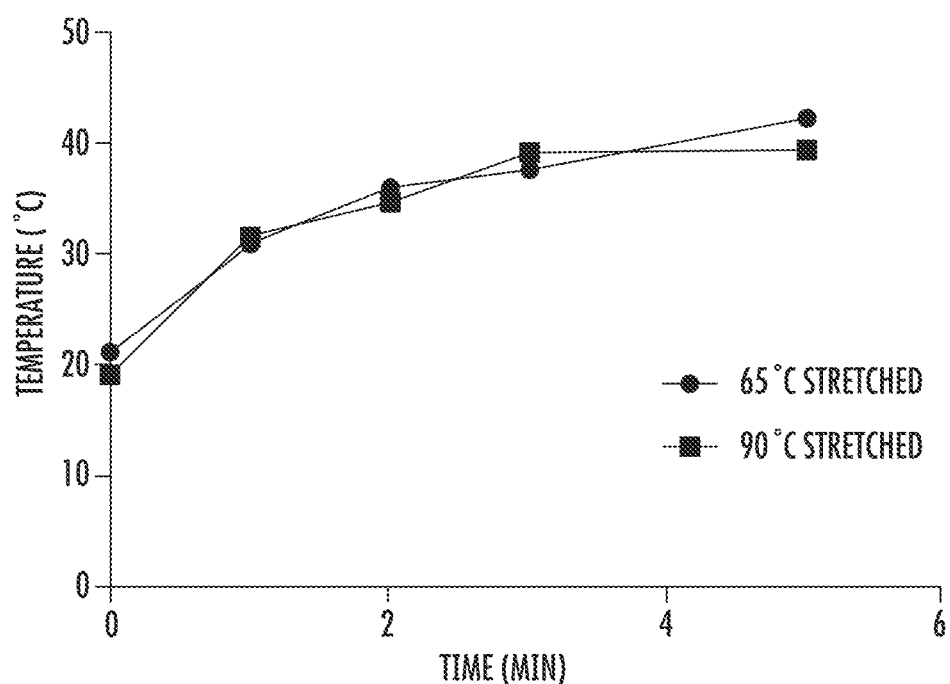
Figure 5F:
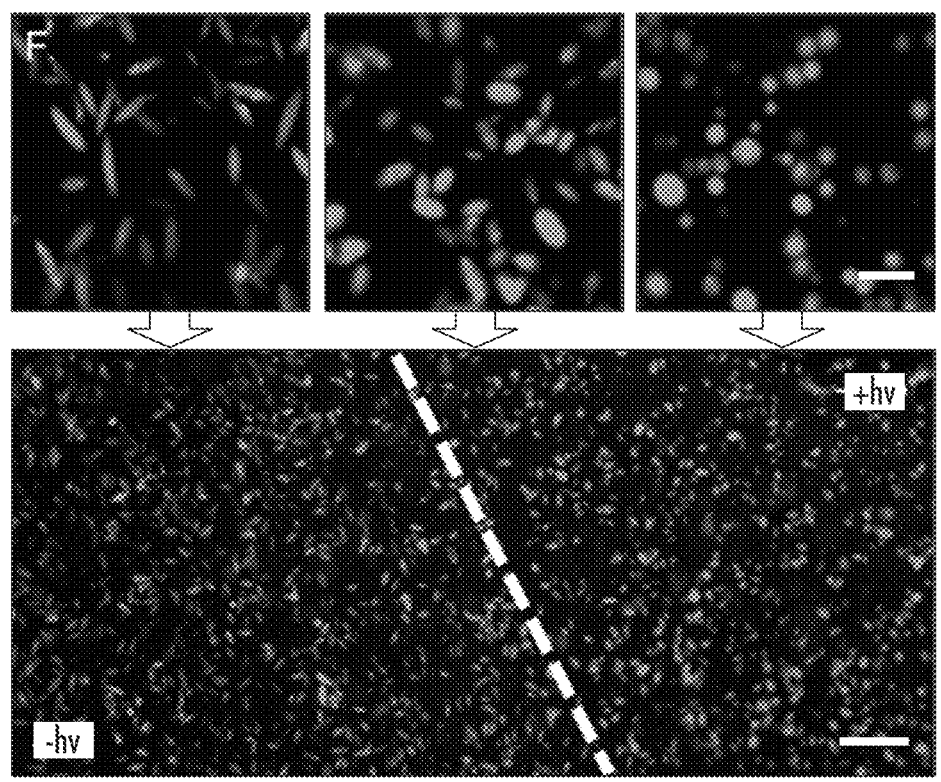
Figure 5G:
Figure 5H:
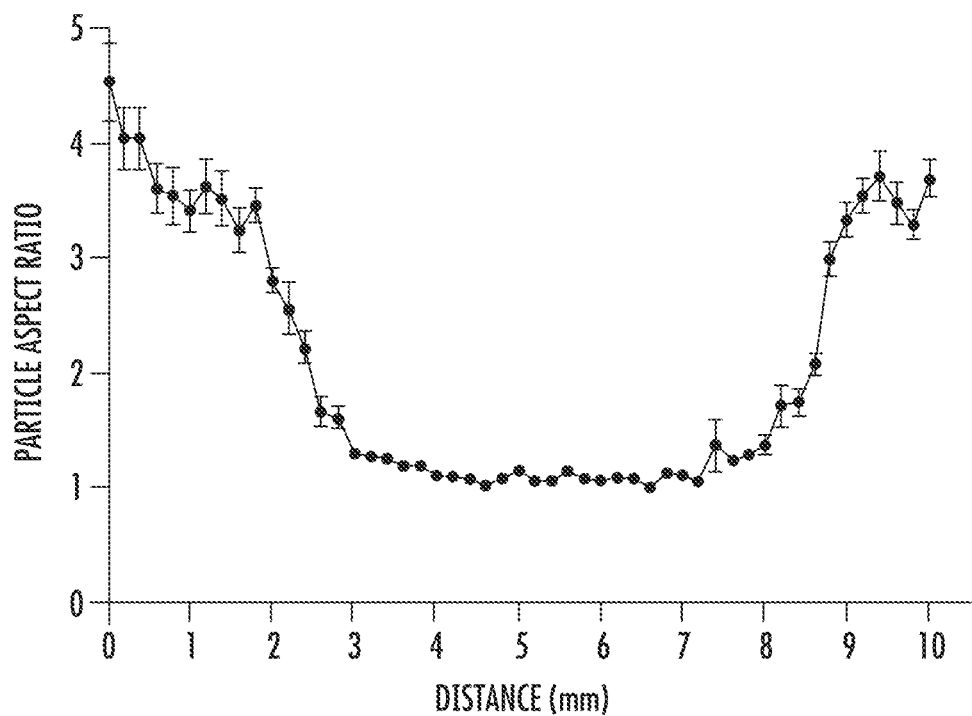
Figure 6A:
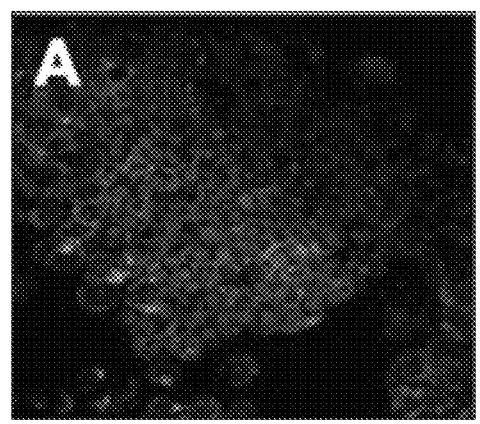
Figure 6B:
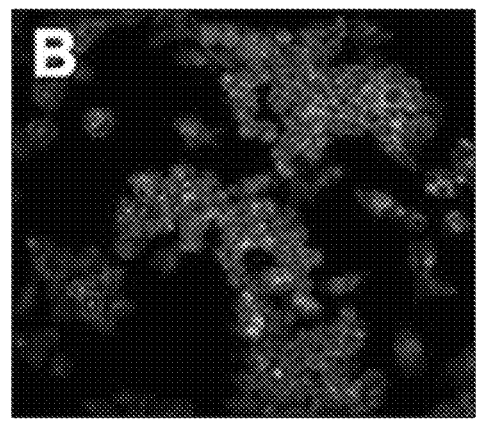
Figure 6C:
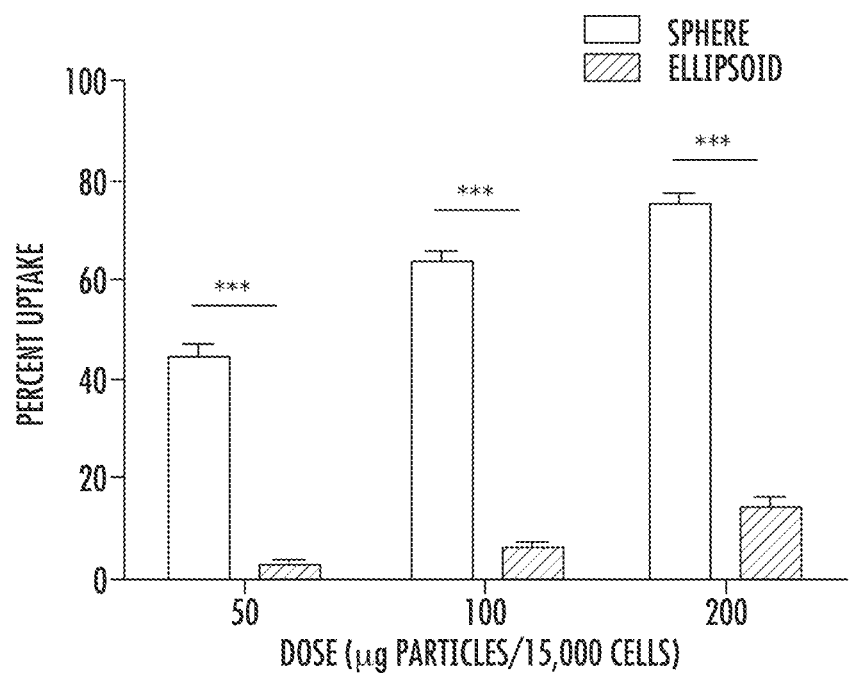
Figure 8A:
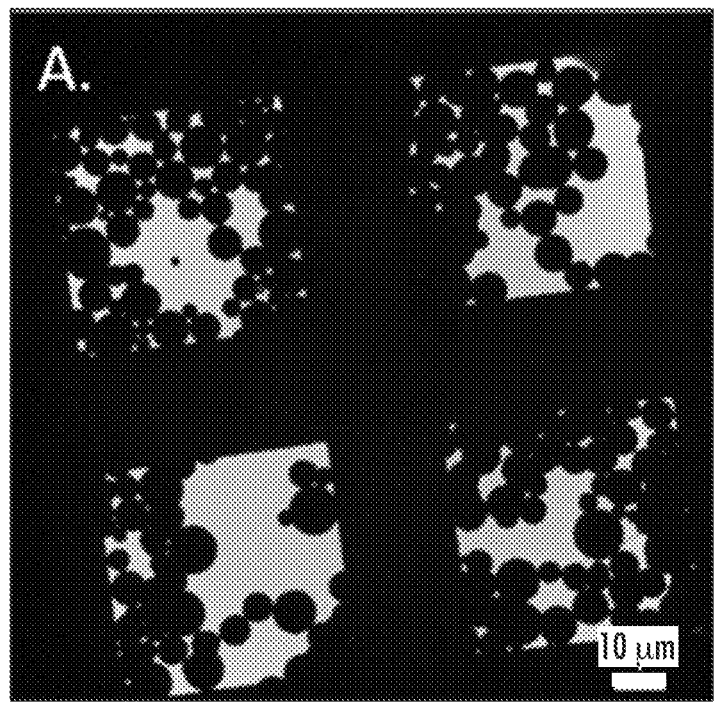
Figure 8B:
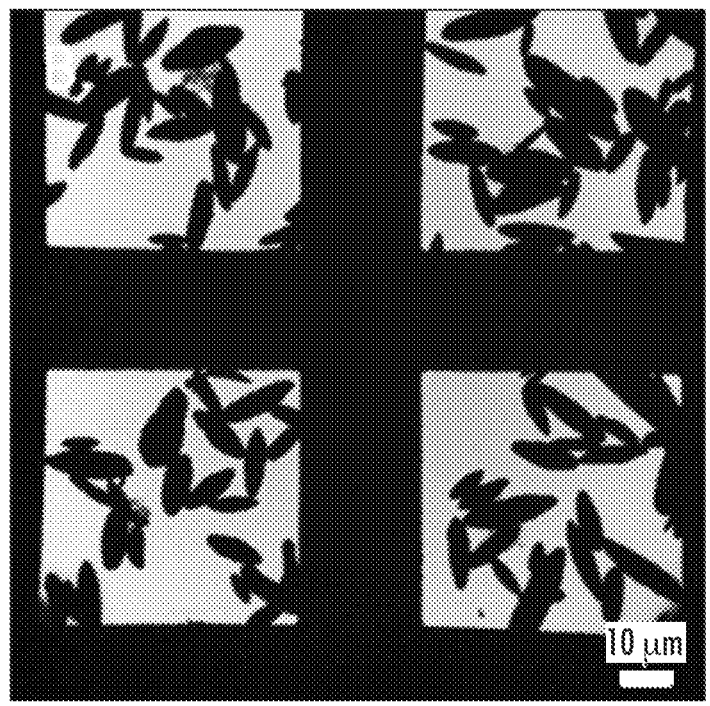
Figure 8C:
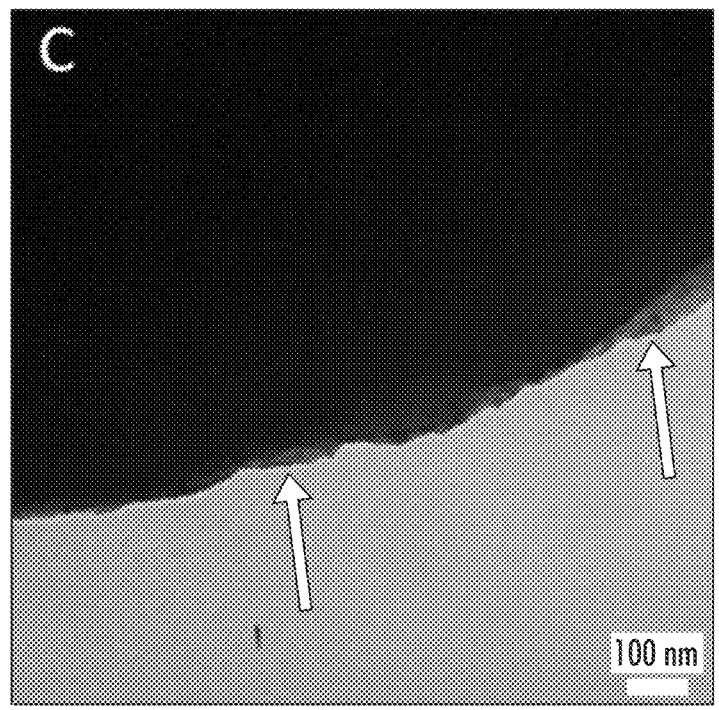
Figure 8D:
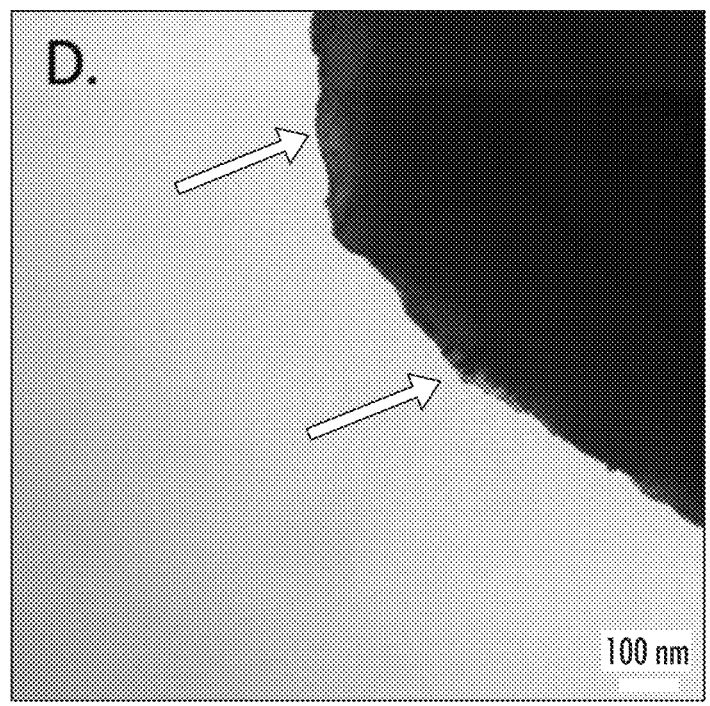
Figure 9:
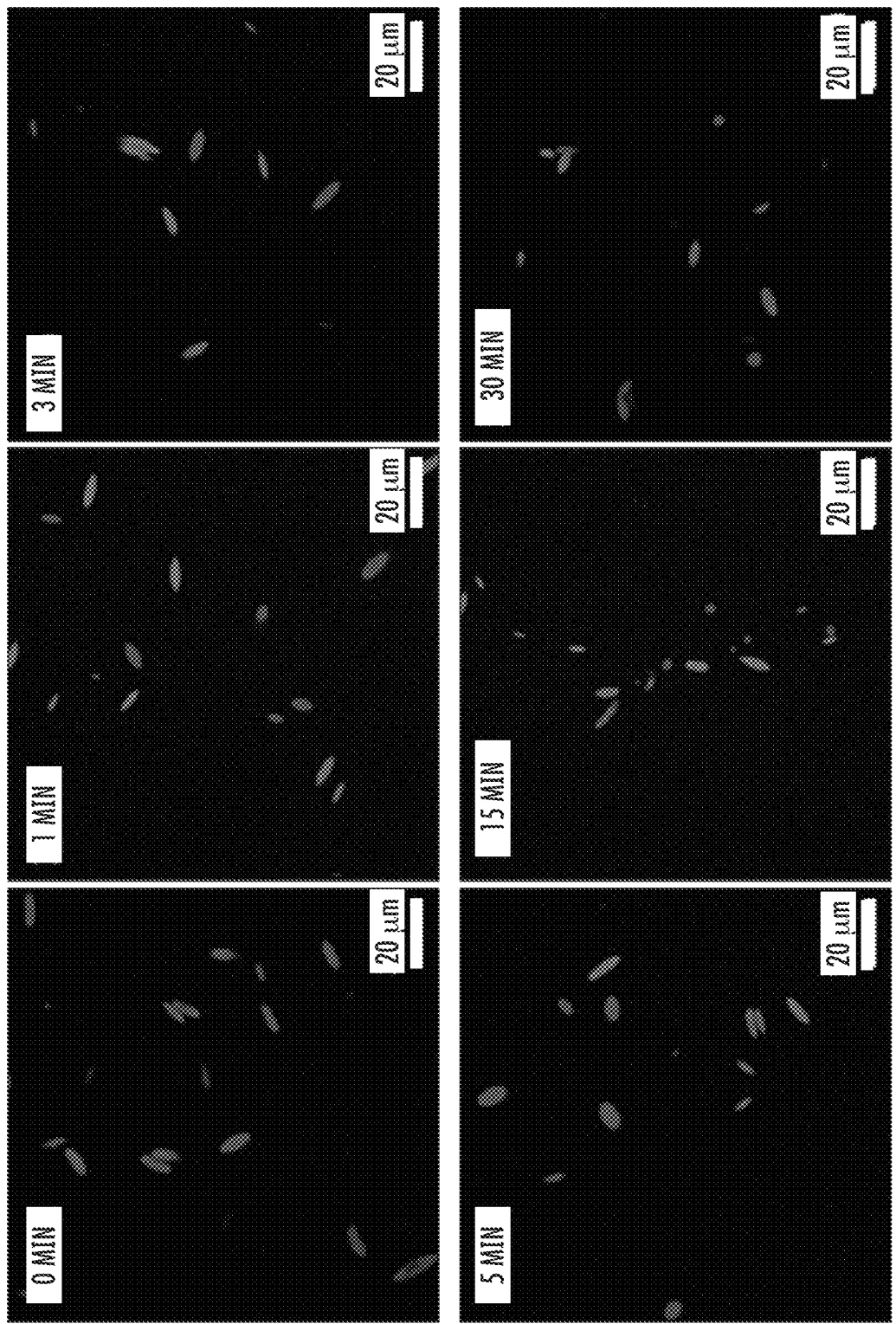
Figure 10:
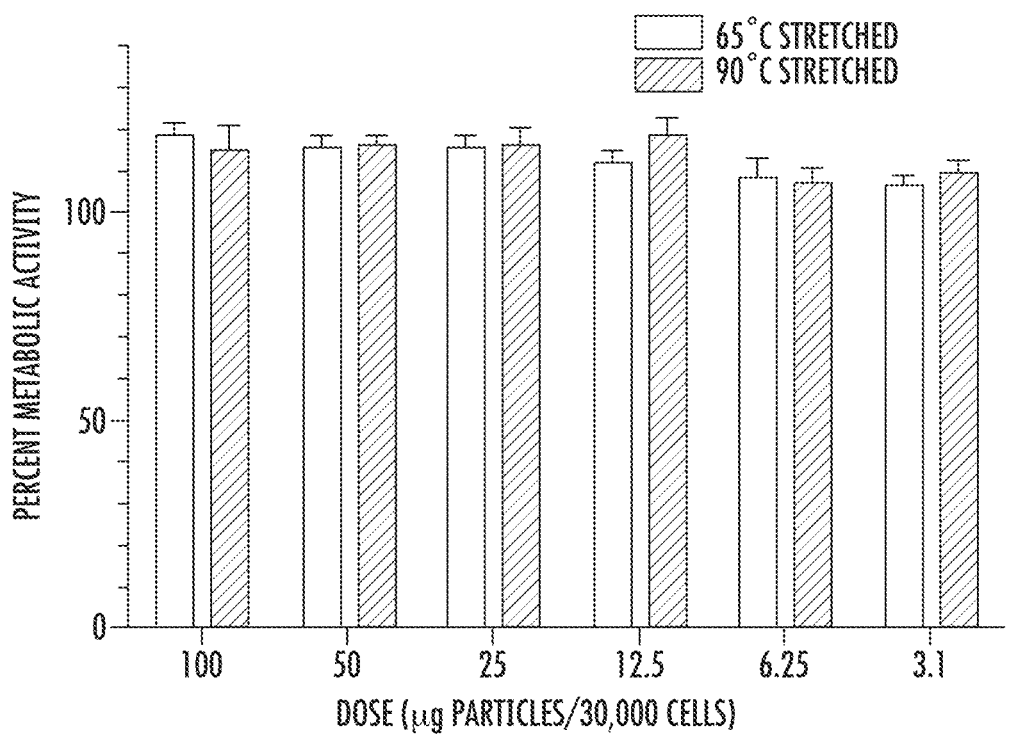
Figure 11:
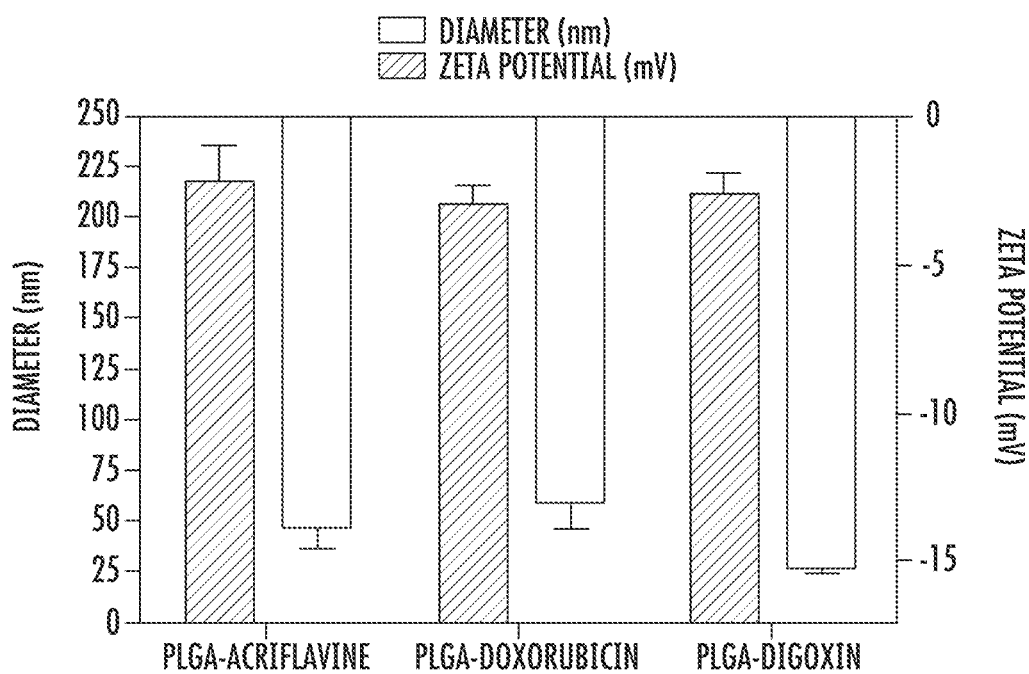
Figure 12:
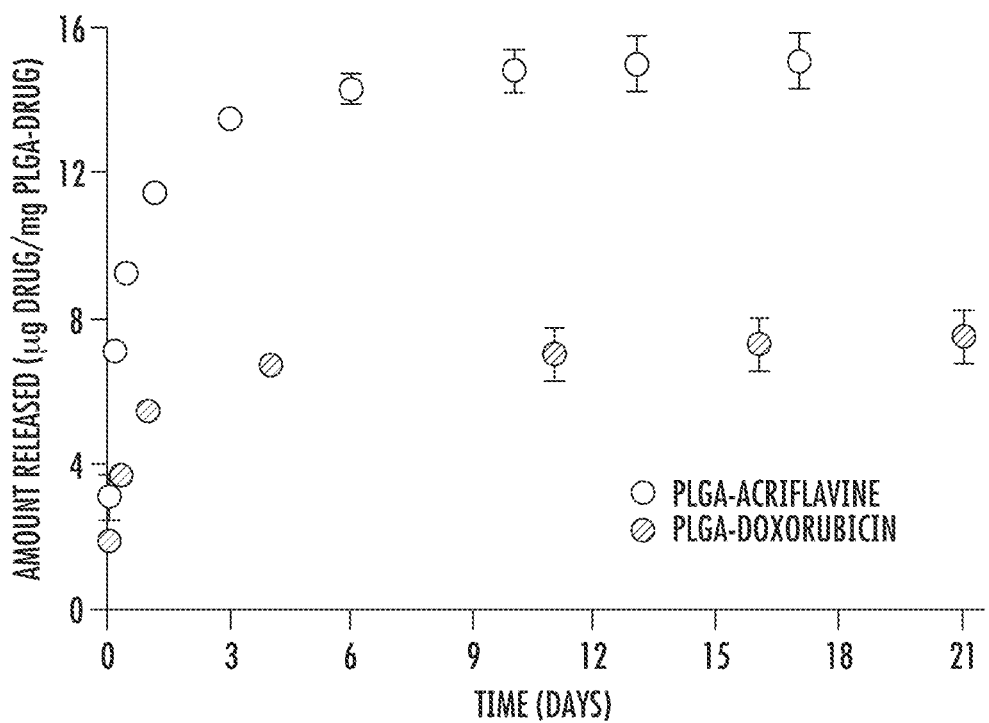
Figure 13:
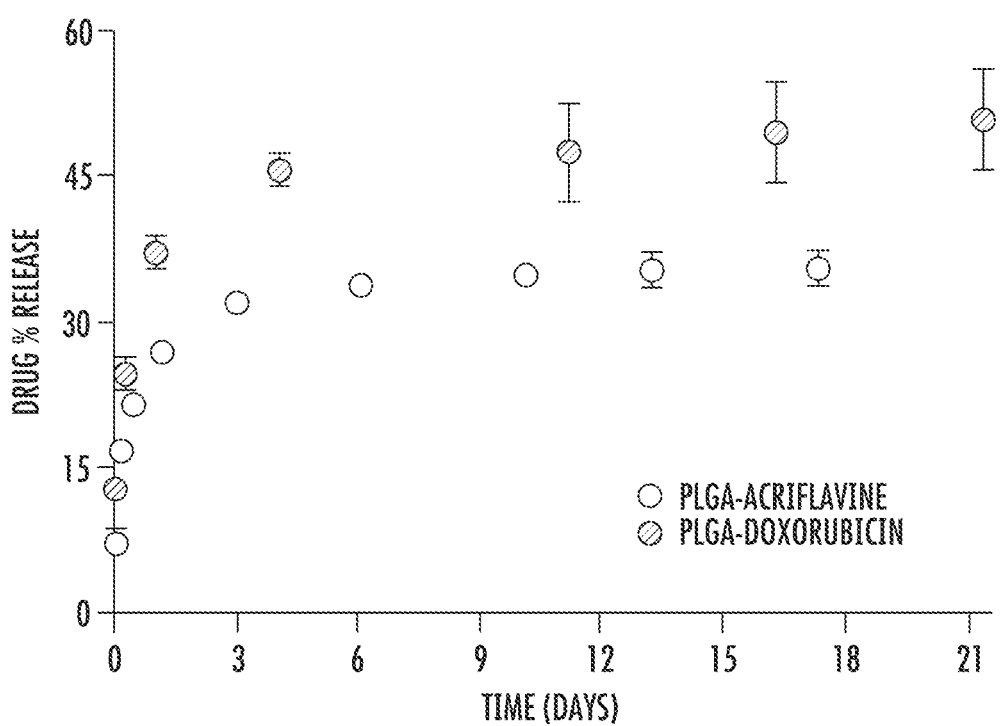
Figure 14:
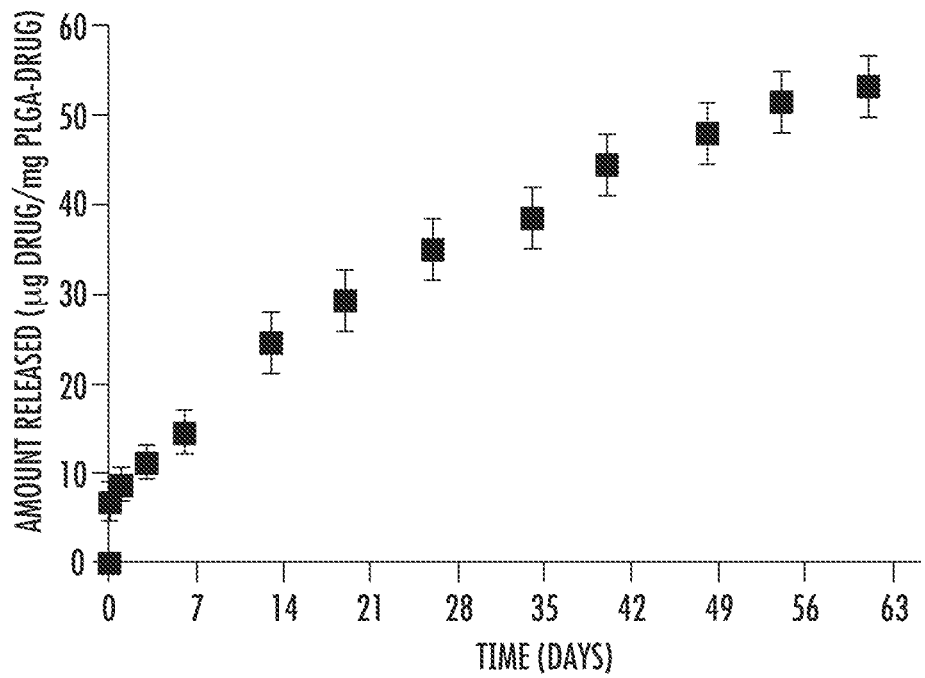
Figure 15:
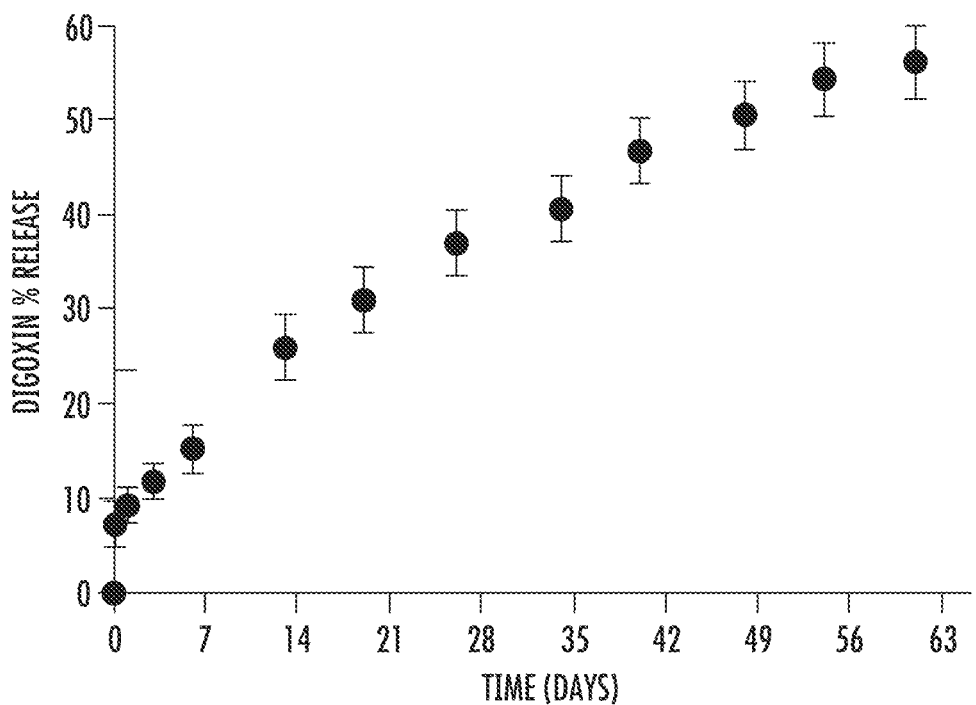
Figure 16A:
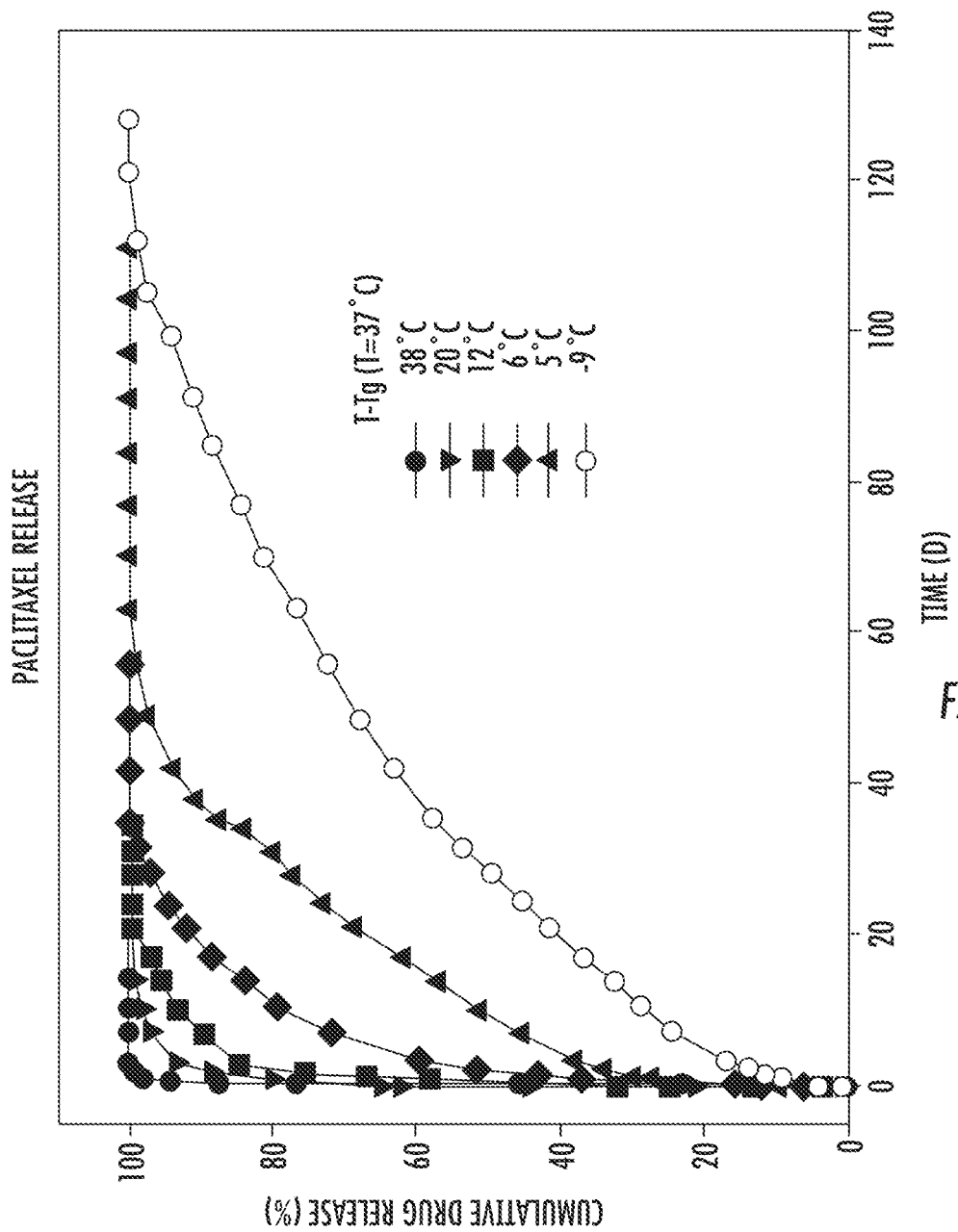
Figure 16B:
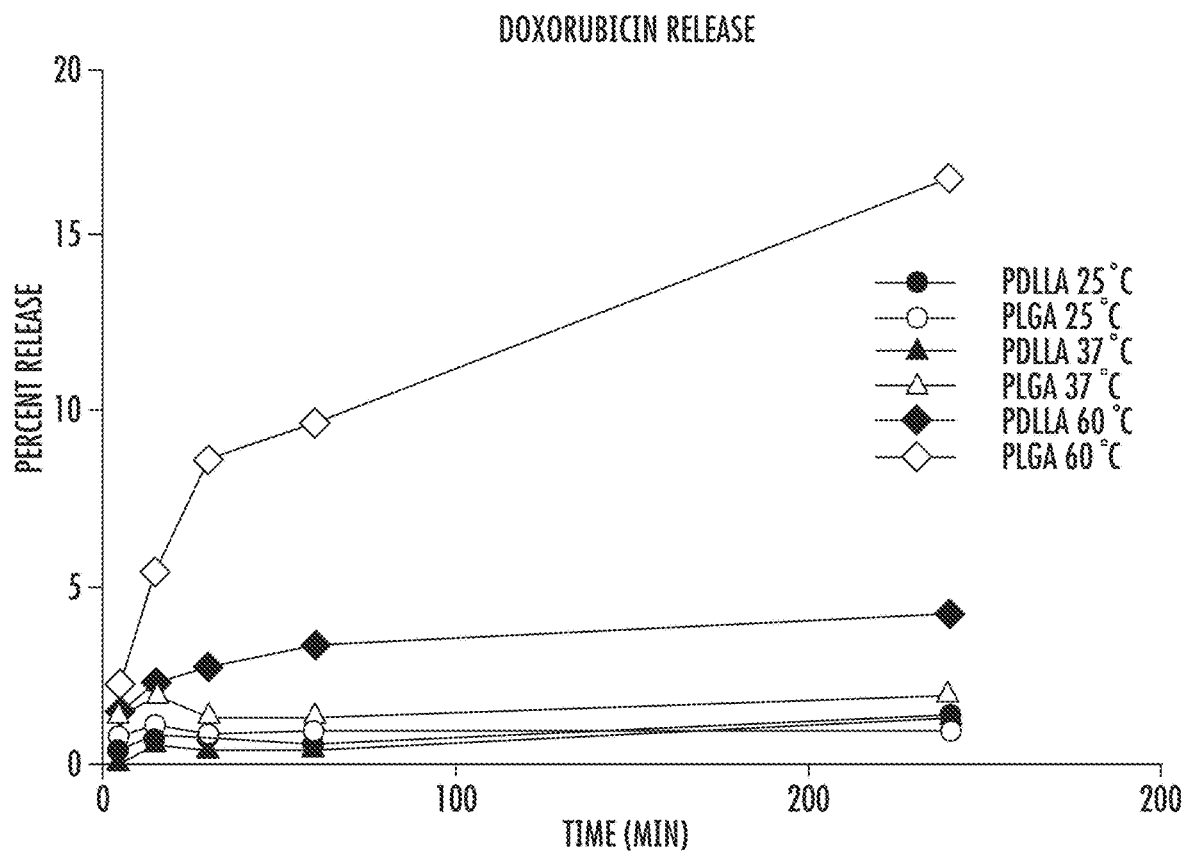
Figure 16C:
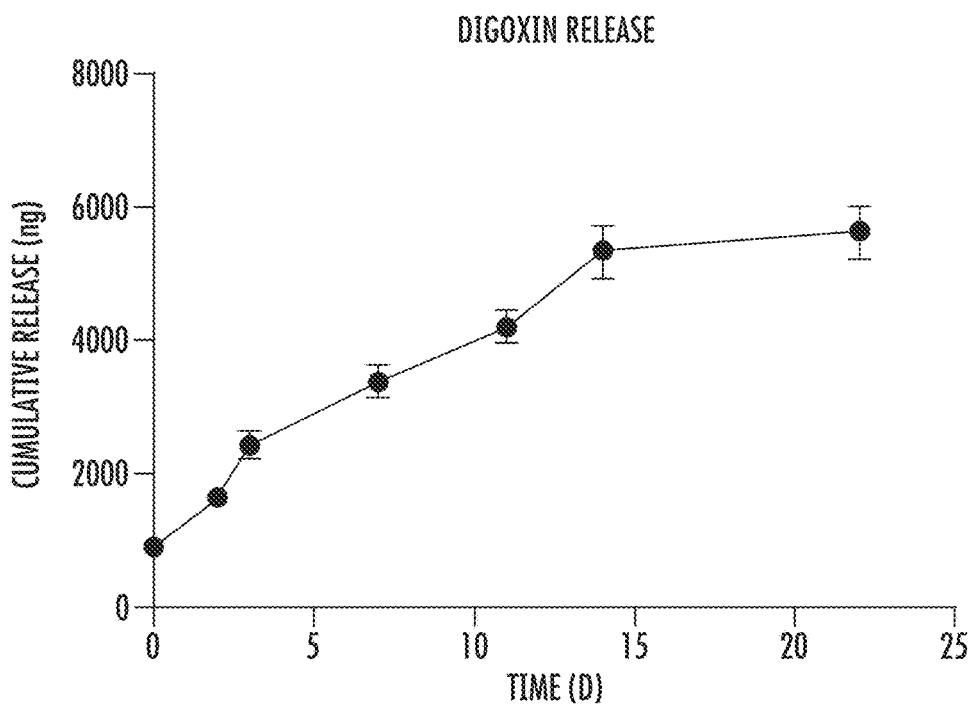
Figure 17A:
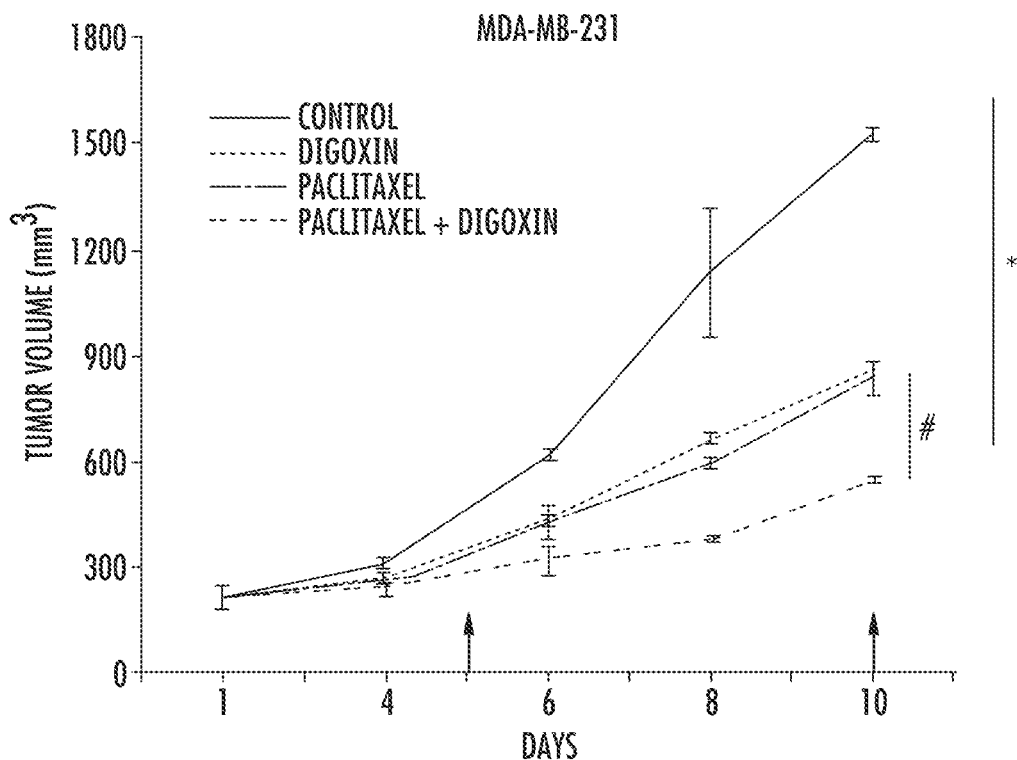
Figure 17B:
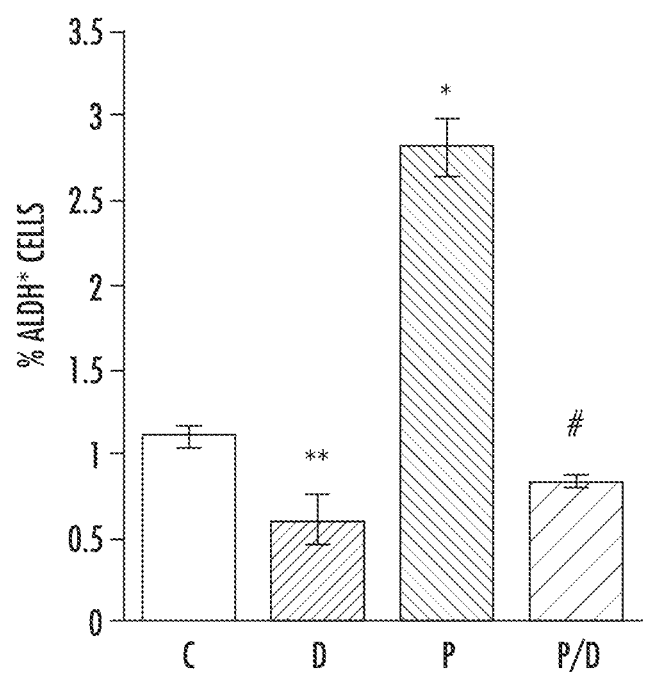
Figure 17C:
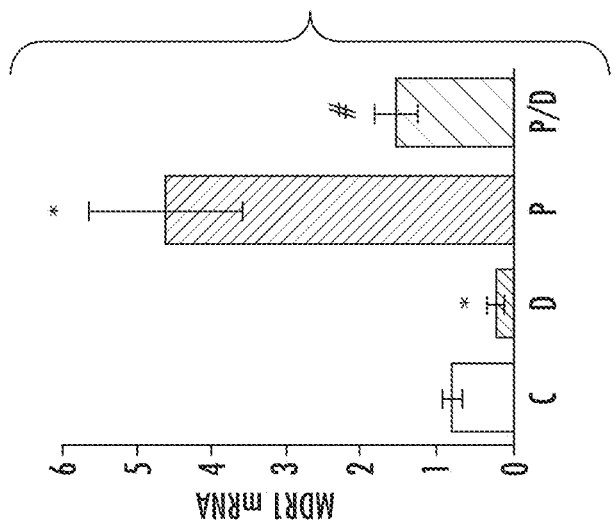
Figure 17C:
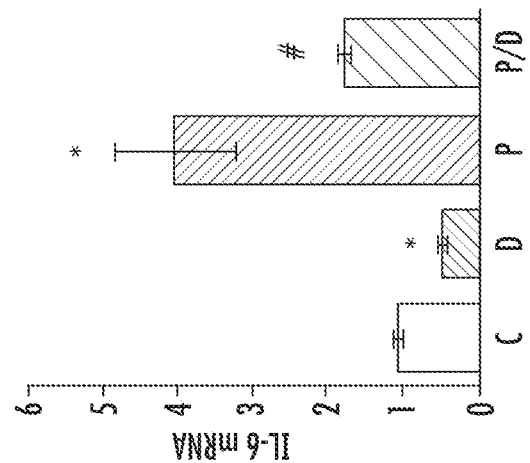
Figure 17C:
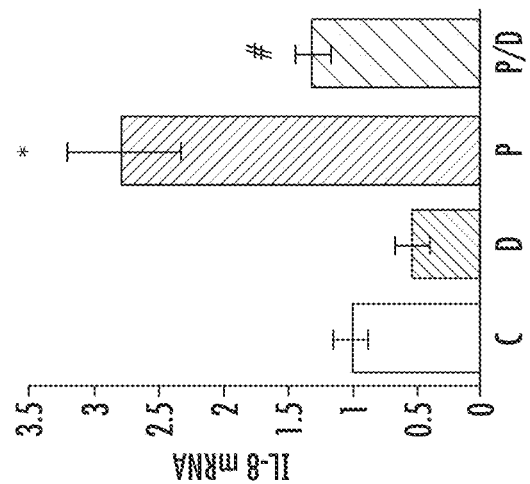
Figure 18:
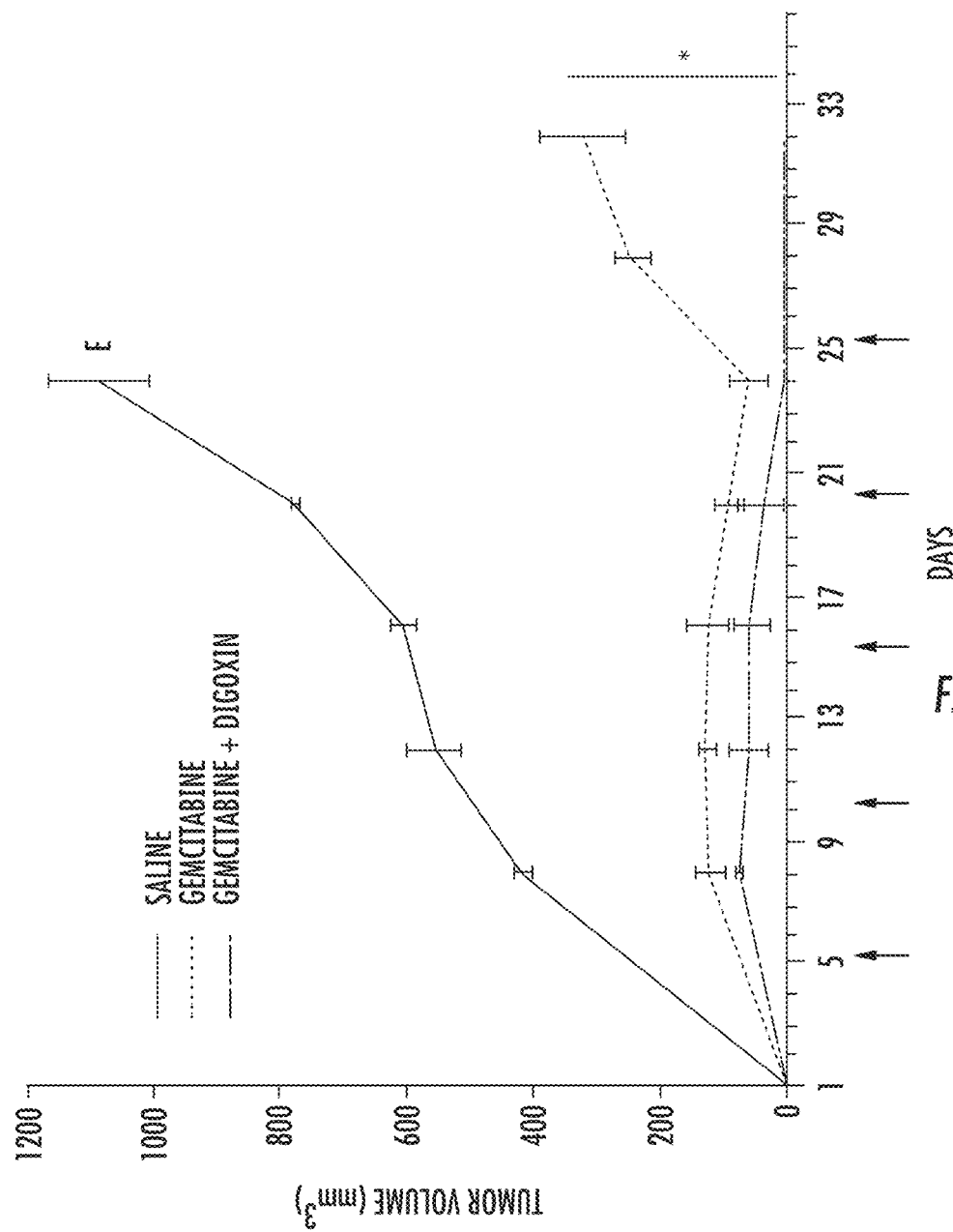

Having thus described the presently disclosed subject matter in general terms, reference will now be made to the accompanying Figures, which are not necessarily drawn to scale, and wherein:

FIG. 1A and FIG. 1B show polymeric particle entropy driven shape memory effect. FIG. 1A shows that Poly (D,L lactic acid) particles were synthesized encapsulating hydrophobic lipid stabilized gold nanoparticles. Due to high molecular weight of the polymer in use, physical crosslinks of the polymer were present in the sample. FIG. 1B shows that polymeric particles are stretched to anisotropic shapes under low or high temperatures and then the entropy driven shape memory effect is triggered by thermal means. Low temperature stretched particles assume their original shape whereas high temperature stretched particles do not;

FIG. 2A, FIG. 2B, FIG. 2C, and FIG. 2D show the shape memory effect of polymeric microparticles. Poly (D,L lactic acid) microparticles (FIG. 2A) were stretched either at 65° C. (FIG. 2B) or 90° C. (FIG. 2C) to an anistropic shape and were then incubated (from left to right) for 1 minute, 5 minutes, 15 minutes, 30 minutes, or 60 minutes and then analyzed under SEM. Image analysis demonstrates the shape memory effect triggered at low temperature stretched particles, but not at high temperature stretched particles. FIG. 2D shows that polymer alignment is present to a higher degree in 65° C. stretched particles as opposed to 90° C. stretched particles indicating polymer physical crosslinks as the driving force behind the observed shape memory effect;

FIG. 3A, FIG. 3B, FIG. 3C, FIG. 3D, and FIG. 3E show characterization of the particles. SEM characterization of spherical (FIG. 3A) and non-spherical (FIG. 3B) particles. FIG. 3C shows size characterization of the spherical particles demonstrating a size of about 4 µm. FIG. 3D and FIG. 3E show absorbance spectrum (FIG. 3D) and standard curve (FIG. 3E) of AuNPs (various concentrations in 1 mL of toluene) in the presence of pure PDLLA microparticles (5 mg in 400 µL of DMSO). The gold nanoparticles were present at 1.63*10 particles/mg particles and the absorbance peak was 530 nm;

FIG. 4A to FIG. 4D show heat activation of shape memory microparticles. Particles were stretched at 60° C. or 90° C.; these particles were incubated in a water bath at three different temperatures (40° C., 45° C., and 50° C.) for up to 30 min;

FIG. 5A, FIG. 5B, FIG. 5C, FIG. 5D, FIG. 5E, FIG. 5F, FIG. 5G, and FIG. 5H show spatiotemporal control of shape memory effect as triggered by laser heating of encapsulated gold nanoparticles. Particles were stretched at 65° C. (FIG. 5A) or 90° C. (FIG. 5B) and lasered by 532 nm laser for (from left to right) 0 minutes, 1 minute, 2 minutes, 3 minutes, or 5 minutes. The shape memory effect was observed in the particles stretched at 65° C. as opposed to 90° C. FIG. 5C shows aspect ratio analysis of the particles in FIG. 5A and FIG. 5B demonstrating reversion of the particles back to spheres (AR=1) within 3 minutes of lasering. FIG. 5D shows normalization as described in Example 1 demonstrating that the particles stretched at 65° C. achieve 100% aspect ratio reversion and the particles at 90° C. achieve ~20% aspect ratio reversion. Error bars are standard error of 20 particles analyzed. FIG. 5E shows that the temperature of the two samples does not differ over the course of heating. FIG. 5F shows that particles immobilized in a PEG hydrogel demonstrate spatial selection of the shape memory effect. The area where the laser was applied is the area where particles achieve shape memory. FIG. 5G shows that the thermal IR image of PEG hydrogel demonstrates heating throughout the entire gel. FIG. 5H shows the aspect ratio analysis of stitched confocal images demonstrating near complete reversion of particles only at the spot where the laser irradiated the particles;

FIG. 6A, FIG. 6B, and FIG. 6C show shape dependence of cellular uptake. FIG. 6A and FIG. 6B show the macrophages' clear preference for uptaking spherical particles (FIG. 6A) over stretched particles (FIG. 6B). FIG. 6C shows confirmation of the preference at varying doses. Blue=DAPI, Green=Actin, Red=Particles;

FIG. 7A, FIG. 7B, and FIG. 7C show that phagocytic cells demonstrate different responses to differentially stretched particles that are triggered by the laser. (FIG. 7A) 65° C. stretched and (FIG. 7B) 90° C. stretched particles were triggered by laser irradiation and incubated with macrophages for 4 hours. Confocal imaging demonstrates that there is a preference of macrophages to phagocytically take up soherical particles in high quantities compared to non-spherical particles. Blue=DAPT, Red=Actin, Green=Particles. FIG. 7C shows that the percent positive uptake as analyzed by flow cytometry demonstrates that the 65° C. stretched laser triggered shape memory particles are taken up at a higher percentage of the course of 4 hours. Error bars are standard error of n=4 replicates;

FIG. 8A, FIG. 8B, FIG. 8C, and FIG. 8D show spherical (FIG. 8A) and non-spherical (FIG. 8B) PDLLA microparticles encapsulating gold nanoparticles imaged under TEM to analyze the presence of gold nanoparticles. Zoomed in pictures of the edges (area of minimal polymer TEM image interference) of spherical (FIG. 8C) and stretched (FIG. 8D) microparticles demonstrate the presence of gold nanoparticles (red arrows) encapsulated within the polymeric microparticle;

FIG. 9 shows a representative mixed particle shape memory experiment. Particles stretched at 65° C. (blue) and particles stretched at 90° C. (pink) were mixed in a 1:1 ratio and heated at 40° C. for the indicated time. Confocal imaging of the subsequent samples demonstrates a sole dependence of the shape memory effect on the particle stretching temperature;

FIG. 10 shows cell viability is not altered by exposure of the cell to various doses. Cell metabolic rate was assessed after 4 hr. of exposure to the particles by MTS assay. The rates were then normalized to untreated cells to give percent metabolic activity. No significant reduction was noted. Error bars are standard error of n=4 replicates;

FIG. 11 shows diameter (n≥2) and zeta potential (n=3) of the PLGA-drug formulations;

FIG. 12 shows PLGA-acriflavine (n=3) and PLGA-doxorubicin (n=2) cumulative release in time [PLGA, poly(D,L-lactide-co-glycolide];

FIG. 13 shows PLGA-acriflavine (n=3) and PLGA-doxorubicin (n=2) percent release in time;

FIG. 14 shows PLGA-digoxin cumulative release in time (n=3);

FIG. 15 shows PLGA-digoxin percent release in time (n=3);

FIG. 16A, FIG. 16B, and FIG. 16C show temperature-dependence of drug release. FIG. 16A shows that paclitaxel release from PLA-based polymers exhibited strong dependence on the difference between drug release temperature and polymer $T_g$. FIG. 16B shows that similar results were also found in doxorubicin release from microparticles. FIG. 16C shows cumulative digoxin release;

FIG. 17A, FIG. 17B, and FIG. 17C show that digoxin blocks paclitaxel-induced enrichment of breast cancer stem cells (BCSCs) in triple-negative breast cancer (TNBC) orthografts. MDA-MB-231 cells were implanted into the mammary fat pad of female severe combined immunodeficiency (Scid) mice. Mice were randomized to four groups, which were treated with: saline (control, C); digoxin (D); paclitaxel (P); or paclitaxel and digoxin (P/D). FIG. 17A shows tumor volumes, which were determined every 2-3 days. Tumors were harvested on day 12 for Aldefluor assay to determine the percentage of aldehyde dehydrogenase-expressing (ALDH$^+$) BCSCs (FIG. 17B) and RT-qPCR assays to quantify the expression of mRNAs encoding interleukin (IL) 8, IL-6, and the multidrug drug resistance protein MDR1 (FIG. 17C). Data are shown as mean+SEM (n=3). *P<0.001 compared with C, and # P<0.001 compared with P, by Student's t test; and FIG. 18 shows that combination therapy of gemcitabine with digoxin prevents tumor relapse. MDA-MB-231 cells were implanted into the mammary fat pad of female Scid mice. When a tumor was palpable (day 1), the mice were randomized to three groups, which were treated with intra-peritoneal injections of: saline, gemcitabine [20 mg/kg on days 5, 10, 15, 20, and 25 (arrows)], or gemcitabine and digoxin (2 mg/kg on days 1-25). Tumor volumes were determined every 2-3 d and mean±SEM (n=3) are shown. The saline-treated mice were euthanized (E) on day 24 when tumor volume exceeded 1,000 mm$^3$. The experiment was terminated on day 32, 7 days after treatment was discontinued. *P<0.001 by Student's t test.

The patent or application file contains at least one drawing executed in color. Copies of this patent or patent application publication with color drawings will be provided by the Office upon request and payment of the necessary fee.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Methods and Compositions Comprising Shape Memory Particles

In some embodiments, the presently disclosed subject matter provides compositions, methods, and kits comprising shape memory particles that are capable of being activated or stimulated to change shape. These shape memory particles can maintain their temporary shape at physiological temperature and switch back to their primary shape upon the application of an external stimulus to a patient. In some embodiments, the drug delivery capacity and shape change capability of the presently disclosed shape memory particles can enhance drug delivery and/or efficacy to a target location inside a patient. Accordingly, in some embodiments, drug delivery can be controlled spatially and/or temporally to mediate delivery of intracellular and extracellular therapeutics. For example, the shape memory particles can be forced to release their load, such as a drug, at a particular time and/or location within a patient. In some embodiments, the presently disclosed shape memory particles can be triggered at a temperature within the body-endurable temperature range, for example, from about 37° C. to about 45° C.

In some embodiments, the presently disclosed subject matter provides a composition comprising an anisotropic shape memory particle comprising a polymeric matrix and at least one stimuli-sensitive nanoparticle. In some embodiments, the presently disclosed subject matter provides a composition comprising an anisotropic shape memory particle comprising a poly(lactic acid)-based polymeric matrix and at least one stimuli-sensitive nanoparticle. As used herein, the term "shape memory particle" refers to a microparticle or a nanoparticle that can undergo a shape transformation upon being triggered by an external stimulus.

The term "anisotropic" refers to a microparticle or nanoparticle that is non-spherical. In some embodiments, the "anisotropic" particle refers to a three-dimensional microparticle or nanoparticle having an asymmetrical shape defined by a dimension (a) along an x-axis, a dimension (b) along a y-axis, and a dimension (c) along a z-axis, wherein at least one of (a), (b), or (c) is not equal to at least one other dimension (a), (b), or (c). In some embodiments, the "anisotropic" particle refers to a three-dimensional microparticle or nanoparticle having an asymmetrical shape, wherein the asymmetrical shape has at least one surface having a radius of curvature along at least one axis selected from one of the following ranges: (a) about 1 nm to about 10 nm; (b) about 11 nm to about 100 nm; (c) about 101 nm to about 400 nm; (d) about 401 nm to about 1 μm; (e) about 10 μm to about 20 μm; (0 about 20 μm to about 100 μm; and (g) about 101 μm to about 1 mm. In some embodiments, the non-spherical shape comprises a prolate ellipsoid, which is defined by the equation a>b=c. In some embodiments, the non-spherical shape comprises a tri-axial ellipsoid, which can be described by the equation a>b>c. In some embodiments, the non-spherical shape comprises an oblate ellipsoid, which can be described by the equation a=b>c. In some embodiments, the non-spherical shape has a dimension (a) along the x axis is equal to the dimension (b) along the y axis, both of which are much less than dimension (c) along the z-axis, such that a=b<<c and the three-dimensional microparticle or nanoparticle comprises a rod.

As used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). In some embodiments, the nanoparticle has at least one dimension, e.g., a diameter, of about 100 nm. In some embodiments, the nanoparticle has a diameter of about 200 nm. In other embodiments, the nanoparticle has a diameter of about 500 nm. In yet other embodiments, the nanoparticle has a diameter of about 1000 nm (1 µm). In such embodiments, the particle also can be referred to as a "microparticle." Thus, the term "microparticle" includes particles having at least one dimension in the range of about one micrometer (µm), i.e., $1\times10^{-6}$ meters, to about 1000 µm. The term "particle" as used herein is meant to include nanoparticles and microparticles. In some embodiments, the anisotropic shape memory particle ranges in size from about 10 nanometers to about 500 microns. In some embodiments, the anisotropic shape memory particle ranges in size from about 50 nanometers to about 5 microns. In some embodiments, the anisotropic shape memory particle is at least 10, 20, 30, 40, or 50 nanometers in size. In some embodiments, the anisotropic shape memory particle is less than 500, 400, 300, 200, 100, 50, or 5 microns in size. In some embodiments, the anisotropic shape memory particles are small enough to have an enhanced permeability and retention (EPR) effect, such that they tend to accumulate in tumor tissue rather than normal tissue. For example, the anisotropic shape memory particles can be less than 400 nanometers in size to take advantage of the EPR effect. In some embodiments, the particles that take advantage of the EPR effect are between about 200 to about 225 nanometers in size. In some embodiments, the anisotropic shape memory particles that take advantage of the EPR effect are less than 200 nanometers in size.

In some embodiments, the microparticle or nanoparticle has an aspect ratio ranging from about 1.1 to about 5. In some embodiments, the aspect ratio has a range from about 5 to about 10. In some embodiments, the aspect ratio has a range from about 10 to about 100.

In some embodiments, non-limiting examples of polymeric matrices include poly(lactic acid)-based polymeric matrices, such as polylactic acid (PLA), poly(D,L-lactide-co-glycolide) (PLGA), and poly (D,L-lactic acid) (PDLLA), as well as non-poly(lactic acid)-based polymeric matrices, such as polycaprolactone (PCL) and poly(beta-amino ester) (PBAE).

As used herein, the term "poly(lactic acid)-based polymeric matrix" refers to a polymeric matrix comprising poly(lactic acid). Non-limiting examples include polylactic acid (PLA), poly(D,L-lactide-co-glycolide) (PLGA) and poly (D,L-lactic acid) (PDLLA). In some embodiments, the poly(lactic acid)-based polymeric matrix comprises PLA. In some embodiments, the poly(lactic acid)-based polymeric matrix comprises PDLLA. In some embodiments, the poly(lactic acid)-based polymeric matrix comprises PLGA. In some embodiments, the poly(lactic acid)-based polymeric matrix comprises more than one type of poly(lactic acid), such as a combination of PDLLA and PLGA.

In some embodiments, the polymeric matrix comprises a copolymer of a poly(lactic acid)-based polymer and a non-poly(lactic acid)-based polymer, such as a combination of PLA and polycaprolactone (PCL). In some embodiments, blends of polyesters may be used such as PLGA/PCL or PLGA/PBAE. In some embodiments, the PLGA content is between about 50 to about 90% with the remainder being PCL and/or PBAE.

As used herein, a "stimuli-sensitive nanoparticle" refers to a nanoparticle that can be activated by an external stimulus. Non-limiting examples of stimuli-sensitive nanoparticles include light-sensitive nanoparticles such as gold nanoparticles, gold nanorods, gold nanospheres, gold nanoshells, and magnetic-sensitive nanoparticles such as iron oxide. In some embodiments, the stimuli-sensitive nanoparticle can be spatially and/or temporally activated. For example, in some embodiments, the stimuli-sensitive nanoparticle can be activated when it reaches the target location inside a patient. As another example, in some embodiments, the stimuli-sensitive nanoparticle can be activated at a certain time after being administered to a patient.

In some embodiments, the presently disclosed subject matter provides a method for using the shape memory particles to deliver a drug to a patient. In some embodiments, a method is provided for delivering a drug to a patient, the method comprising: (a) administering to a patient an anisotropic shape memory particle comprising a polymeric matrix and at least one stimuli-sensitive nanoparticle, wherein the anisotropic shape memory particle is loaded with at least one drug; and (b) stimulating the at least one stimuli-sensitive nanoparticle to release the at least one drug from the anisotropic shape memory particle at a target location inside the patient. As used herein, a "drug" is a substance that has a physiological effect when introduced into a subject.

In some embodiments, stimulating at least one stimuli-sensitive nanoparticle to release a drug occurs by stimulating the patient. In some embodiments, stimulating at least one stimuli-sensitive nanoparticle to release the drug occurs external of the patient. Non-limiting examples of stimuli that can be used to stimulate or activate the stimuli-sensitive nanoparticle include heat, light (e.g., a laser beam), and electricity. In some embodiments, the activation temperature of the presently disclosed shape memory particles is effectively manipulated by efficient local heating inside shape memory particles using stimuli-sensitive nanoparticles. For example, in some embodiments, light from a laser is externally applied to a location on the patient and heat from the light activates stimuli-sensitive nanoparticles in the patient, causing shape memory particles that had previously been administered to the patient and targeted to a target location within the patient to change shape and release their drug load. In some embodiments, more than one kind of drug is loaded into a presently disclosed particle, such that a drug mixture can be simultaneously administered to the patient.

In some embodiments, the presently disclosed subject matter provides a method for treating a disease or disorder in a patient in need thereof, the method comprising: (a) administering to a patient an anisotropic shape memory particle comprising a polymeric matrix and at least one stimuli-sensitive nanoparticle, wherein the anisotropic shape memory particle is loaded with at least one drug that is capable of treating a disease or disorder; and (b) stimulating at least one stimuli-sensitive nanoparticle to release at least one drug from the anisotropic shape memory particle at a target location inside the patient, thereby treating the disease or disorder in the patient.

In some embodiments, the disease or disorder that can be treated can be any disease that can be targeted by a presently disclosed particle comprising a drug to treat the disease or disorder. Non-limiting examples of diseases and disorders include cardiovascular disease, infectious and parasitic disease, cancer, respiratory disease, digestive disease, neurodegenerative disease, immune system disorders, musculoskeletal disorders, ocular disease, and the like.

In some embodiments, a presently disclosed particle is biodegradable and/or biocompatible in the patient. As used herein, "biodegradable" compounds are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. As used herein, the term "biocompatible" means that the compound does not cause toxicity or adverse biological reaction in a patient when administered at a reasonable dose.

Generally, to be biodegradable, the presently disclosed materials, e.g., microparticles and/or nanoparticles, contain a degradable linkage. Representative degradable linkages include, but are not limited to:

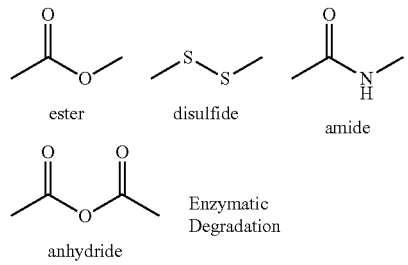

Non-limiting examples of biodegradable polymers include biodegradable poly-β-amino-esters (PBAEs), poly (amido amines), polyesters, polyanhydrides, bioreducible polymers, and other biodegradable polymers. Non-limiting examples of biodegradable polymers include poly(D,L-lactide-co-glycolide) (PLGA), poly (D,L-lactic acid) (PDLLA), polycaprolactone (PCL), polyglycolic acid (PGA), polylactic acid (PLA), poly(acrylic acid) (PAA), poly-3-hydroxybutyrate (P3HB) and poly(hydroxybutyrate-co-hydroxyvalerate). Other biodegradable polymers suitable for use with the presently disclosed subject matter are provided in International PCT Patent Application Publication No. WO/2010/132879 for "Multicomponent Degradable Cationic Polymers," to Green et al., published Nov. 18, 2010, which is incorporated herein by reference in its entirety. In some embodiments, nondegradable polymers that are used in the art, such as polystyrene, are blended with a biodegradable polymer or polymers to form a presently disclosed particle. In some embodiments, a presently disclosed particle comprises GRAS (Generally Regarded As Safe) materials. In some embodiments, the polymeric matrix is poly(lactic acid)-based.

In some embodiments, the surface of a presently disclosed particle comprises at least one biomolecule comprising a targeting agent and/or a therapeutic agent. Non-limiting examples of a targeting agent include a sugar, peptide, antibody or antibody fragment, hormone, hormone receptor, receptor ligand, and the like. In some embodiments, the targeting agent is a moiety that has affinity for a tumor associated factor, such as RGD sequences, low-density lipoprotein sequences, a NAALADase inhibitor, epidermal growth factor, and other agents that bind with specificity to a target cell (e.g., a cancer cell). In some embodiments, the targeting agent is a moiety that has affinity for an inflammatory factor (e.g., a cytokine or a cytokine receptor moiety (e.g., TNF-α receptor)). Antibodies can be generated to allow for the targeting of antigens or immunogens (e.g., tumor, tissue or pathogen specific antigens) on various biological targets (e.g., pathogens, tumor cells, and normal tissue). Such antibodies include, but are not limited to polyclonal, monoclonal, chimeric, single chain, Fab fragments, and a Fab expression library.

Non-limiting examples of therapeutic agents include small molecules, such as small organic or inorganic molecules; saccharides; oligosaccharides; polysaccharides; a biological macromolecule selected from the group consisting of peptides, proteins, peptide analogs and derivatives; peptidomimetics; nucleic acids, such as DNA, RNA interference molecules, selected from the group consisting of siRNAs, shRNAs, antisense RNAs, miRNAs, and ribozymes, dendrimers and aptamers; antibodies, including antibody fragments and intrabodies; and any combination thereof.

In some embodiments, the targeting agent and/or therapeutic agent is a small organic molecule, carbohydrate, sugar, protein, peptide, nucleic acid, antibody or antibody fragment thereof, hormone, hormone receptor, receptor ligand, or cancer cell specific ligand. In some embodiments, a presently disclosed particle comprises more than one type of targeting agent and/or therapeutic agent.

As used herein, the term "small molecule" can refer to agents that are "natural product-like," however, the term "small molecule" is not limited to "natural product-like" agents. Rather, a small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some cases it is preferred that a small molecule have a molecular weight equal to or less than 700 Daltons.

As used herein, an "RNA interference molecule" refers to an agent which interferes with or inhibits expression of a target gene or genomic sequence by RNA interference (RNAi). Such RNA interfering agents include, but are not limited to, nucleic acid molecules including RNA molecules which are homologous to the target gene or genomic sequence, or a fragment thereof, short interfering RNA (siRNA), short hairpin or small hairpin RNA (shRNA), microRNA (miRNA) and small molecules which interfere with or inhibit expression of a target gene by RNA interference (RNAi).

The term "polynucleotide" is used herein interchangeably with "nucleic acid" to indicate a polymer of nucleosides. Typically a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided.

The term "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a non-polypeptide moiety covalently or non-covalently associated therewith is still considered a "polypeptide". Exemplary modifications include glycosylation and palmitoylation. Polypeptides may be purified from natural sources, produced using recombinant DNA technology, synthesized through chemical means such as conventional solid phase peptide synthesis, etc.

As used herein, the term "antibody" refers to a polypeptide or group of polypeptides which comprise at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', F(ab)$_2$, and F(ab')$_2$ fragments.

In some embodiments, the presently disclosed methods further comprise targeting the presently disclosed particles to a target location inside the patient. In some embodiments, the target location within the patient may be any site that the shape memory particles are capable of being targeted to, particularly a diseased site. Non-limiting examples of target locations include the brain, colon, breasts, prostate, liver, kidneys, lungs, esophagus, head and neck, ovaries, cervix, stomach, colon, rectum, bladder, uterus, testes, and pancreas.

In some embodiments, the target location is a cancer site. A "cancer site" in a patient refers to a site showing the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. Non-limiting examples of cancer that can be treated with the presently disclosed shape particles include brain, colon, breast, prostate, liver, kidney, lung, esophagus, head and neck, ovarian, cervical, stomach, colon, rectal, bladder, uterine, testicular, and pancreatic. In some embodiments, the target location is a solid tumor. A "solid tumor", as used herein, is an abnormal mass of tissue that generally does not contain cysts or liquid areas. As used herein, the terms "metastasis" and "metastatic site" refer to a cancer resulting from the spread of a primary tumor. Non-limiting examples of solid tumor and/or metastatic sites that can be treated with the presently disclosed particles include the brain, colon, breast, prostate, liver, kidney, lung, esophagus, head and neck, ovaries, cervix, stomach, colon, rectum, bladder, uterus, testicle, and pancreas.

In some embodiments, the presently disclosed method further comprises stretching the presently disclosed particles to form anisotropic shape memory particles. For example, in some embodiments, the method includes stretching a shape memory particle comprising a polymeric matrix and at least one stimuli-sensitive nanoparticle to form an anisotropic shape memory particle. In some embodiments, the polymeric matrix is stretched without stimuli-sensitive nanoparticles. In some embodiments, the polymeric matrix is stretched with stimuli-sensitive nanoparticles. In some embodiments, the polymeric matrix is stretched without the stimuli-sensitive nanoparticles and the stimuli-sensitive nanoparticles are administered separately from the stretched polymeric matrix into a patient. Methods and devices for stretching can be found in Meyer et al. (*J. Biomed. Mater. Res. A*. 2015, 103(8):2747-57), which is incorporated herein by reference in its entirety.

In some embodiments, the polymeric matrix is stretched at a temperature from above the polymer transition temperature up to the polymer degradation temperature to form an anisotropic polymeric matrix. In some embodiments, the polymeric matrix is stretched at a temperature above but close to the polymer transition temperature. For example, in some embodiments, if the polymer transition temperature is about 60° C., the polymeric matrix is stretched at a temperature above 60° C. to about 70° C. In some embodiments, if the polymer transition temperature is about 60° C., the polymeric matrix is stretched at a temperature above 60° C. to about 80° C. As used herein, the "polymer transition temperature" is the temperature range where the polymer transitions from a hard material to a soft or rubber-like material. As used herein, the "polymer degradation temperature" is the temperature where the polymer begins to disintegrate. In some embodiments, the polymeric matrix is stretched at a temperature from about 60° C. to about 90° C. to form an anisotropic polymeric matrix. In some embodiments, the polymeric matrix is stretched at a temperature of about 60° C.

In some embodiments, stretching the polymeric matrix causes the polymeric matrix to change from a generally spherical shape to an anisotropic shape. In some embodiments, the activation of the at least one stimuli-sensitive nanoparticle induces the shape of the anisotropic shape memory particle to change, such as from an anisotropic shape to another anisotropic shape or a generally spherical shape. In some embodiments, the change in shape of the anisotropic shape memory particle can simultaneously happen with the release of at least one drug molecule from the anisotropic shape memory particle. In some embodiments, the release of at least one drug molecule occurs in a range from about 1 day to about two months after the anisotropic shape memory particle changes shape. In some embodiments, the release of the drug from the shape memory particle occurs after 1, 2, 3, 4, 5, 6, 7 or more days. In some embodiments, the release of the drug from the shape memory particle occurs after 1, 2, 3, 4, 5, 6, 7, 8 or more weeks.

In some embodiments, the change in shape of the anisotropic shape memory particle occurs in a patient. In some embodiments, the stimulus is applied external to the patient in proximity to a target location within the patient, such as in proximity to a solid tumor and/or a metastatic site. In some embodiments, the patient is stimulated by at least one stimulus selected from the group consisting of heat, light, and electricity. In some embodiments, the stimulation of the patient induces the shape of the anisotropic shape memory particle to change, such as from an anisotropic shape to another anisotropic shape or a generally spherical shape.

In some embodiments, the presently disclosed shape memory particles can control cellular responses through shape transformation. For example, it has been found that there is a macrophage phagocytic preference for spherical particles rather than the presently disclosed anisotropic particles, suggesting that the presently disclosed anisotropic particles are more likely to successfully evade the immune system while moving to their target location.

As used herein, the term "treating" can include reversing, alleviating, inhibiting the progression of, preventing or reducing the likelihood of the disease, disorder, or condition to which such term applies, or one or more symptoms or manifestations of such disease, disorder or condition. In some embodiments, "treating" means prolonging survival of patients, such as those having cancer.

In some embodiments, the methods comprising the presently disclosed particles reduce the likelihood of tumor progression and/or mediate tumor regression. For example, the methods comprising the presently disclosed particles (administered either alone or as part of a multi-drug or multi-modality cancer therapy) can reduce the likelihood of tumor progression and/or mediate tumor regression by at least 5%, 10%, 15%, 20%, 25%, 30%, 33%, 35%, 40%, 45%, 50%, 55%, 60%, 66%, 70%, 75%, 80%, 85%, 90%, 91%, 92%, 93%, 94%, 95%, 96%, 97%, 98%, 99% or more as compared to the likelihood of tumor progression and/or tumor regression in the patient when the methods comprising the presently disclosed particles are not used.

In some embodiments, methods comprising the presently disclosed particles extend survival of the patient. For example, the presently disclosed methods can extend survival (e.g., progression free survival) of the patient by 5%, 10%, 15%, 20%, 25%, 30%, 33%, 35%, 40%, 45%, 50%, 55%, 60%, 66%, 70%, 75%, 80%, 85%, 90%, 91%, 92%, 93%, 94%, 95%, 96%, 97%, 98%, 99%, 1-fold, 1.1-fold, 1.2-fold, 1.3-fold, 1.4-fold, 1.5-fold, 1.6-fold, 1.7-fold, 1.8-fold, 1.9-fold, 2.0 fold, 2.5-fold, 3.0-fold, 3.5-fold, 4.0-fold, 5.0-fold, 6-fold, 7-fold, 8-fold, 9-fold, 10-fold, or more as compared to survival of the patient when the presently disclosed methods are not used. In some embodiments, the survival is progression-free survival.

The presently disclosed subject matter provides for the use of a composition comprising an anisotropic shape memory particle comprising a polymeric matrix and at least one stimuli-sensitive nanoparticle for the treatment of a disease or disorder. The presently disclosed subject matter also provides for the use of a composition comprising an anisotropic shape memory particle comprising a poly(lactic acid)-based polymeric matrix and at least one stimuli-sensitive nanoparticle for the treatment of a disease or disorder. In addition, the use of a composition comprising an anisotropic shape memory particle comprising a polymeric matrix and at least one stimuli-sensitive nanoparticle for the manufacture of a medicament for the treatment of a disease or disorder is provided. Further, the use of a composition comprising an anisotropic shape memory particle comprising a poly(lactic acid)-based polymeric matrix and at least one stimuli-sensitive nanoparticle for the manufacture of a medicament for the treatment of a disease or disorder is also provided.

II. Methods for Inhibiting a Hypdxia-Inducible Factor (HIF) and Treating a Hypdxia-Associated Disease or Disorder In some embodiments, the presently disclosed subject matter provides compositions, kits, and methods for delivering hypoxia-inducible factor (HIF) inhibitors to a target location inside a patient to treat a hypoxia-associated disease or disorder. In some embodiments, shape memory particles are used to deliver the HIF inhibitors. In some embodiments, nanoparticles without shape memory are used to deliver the HIF inhibitors. In some embodiments, delivery of the HIF inhibitors is controlled spatially and/or temporally.

In some embodiments, the presently disclosed subject matter provides a composition comprising a nanoparticle comprising a polymeric matrix and at least one hypoxia-inducible factor (HIF) inhibitor. In some embodiments, the presently disclosed subject matter provides a composition comprising a nanoparticle comprising a poly(lactic acid)-based polymeric matrix and at least one hypoxia-inducible factor (HIF) inhibitor. In some embodiments, the poly(lactic acid)-based polymeric matrix comprises PLA. In some embodiments, the poly(lactic acid)-based polymeric matrix comprises PDLLA. In some embodiments, the poly(lactic acid)-based polymeric matrix comprises PLGA.

In some embodiments, the HIF is any HIF or subunit thereof, such as hypoxia-inducible factor-1α (HIF-1α), hypoxia-inducible factor-1β (HIF-1β), hypoxia-inducible factor-2α (HIF-2α), or hypoxia-inducible factor-3α (HIF-3α). In some embodiments, the HIF is HIF-1. In some embodiments, the HIF is HIF-2. In some embodiments, the HIF is HIF-3. In some embodiments, the HIF is HIF-1 and HIF-2. In some embodiments, the HIF is HIF-1, HIF-2, and HIF-3.

In some embodiments, the HIF inhibitor is any HIF inhibitor that can be loaded into a presently disclosed particle. In some embodiments, the HIF inhibitor is an HIF-1 inhibitor such as an HIF-1α mRNA inhibitor (e.g., aminoflavone), an HIF-1α protein synthesis inhibitor (e.g., mTOR inhibitor, cardiac glycoside, microtubule targeting agent, topoisomerase inhibitor, oligonucleotide, aminoflavone, PX-478), an HIF-1α protein stabilization inhibitor (e.g., HSP90 inhibitor, HDAC inhibitor, antioxidant, oligonucleotide, berberine, SE-methylselenocysteine, PX-12, YC-1), an HIF-1α: HIF-1β dimerization inhibitor (e.g., acriflavine, trypaflavine, proflavine), an HIF-1 DNA binding inhibitor (e.g., anthracycline, echinomycin), or an HIF-1 transactivation inhibitor (e.g., bortezomib). In some embodiments, the HIF inhibitor is a cardiac glycoside, such as oleandrin, ouabain, bufalin, digitoxin, digoxin, cinobufatalin, cinobufagin, resibufogenin, deslanoside, digitalin, digitalis, proscillaridin, and the like. In some embodiments, the HIF inhibitor is an anthracycline, such as actinomycin, dactinomycin, daunorubicin (daunomycin), doxorubicin (adriamycin), epirubicin, idarubicin, mitoxantrone, valrubicin, and the like. In some embodiments, the HIF inhibitor is a cardiac glycoside, an anthracycline, or an HIF-1 dimerization inhibitor. In some embodiments, the HIF inhibitor is digoxin or acriflavine.

In some embodiments, the nanoparticle or anisotropic nanoparticle comprising at least one HIF inhibitor, or the nanoparticle or anisotropic nanoparticle comprising a polymeric matrix and at least one HIF inhibitor ranges in size from about 10 nanometers to about 500 microns. In some embodiments, the nanoparticle or anisotropic nanoparticle comprising at least one HIF inhibitor, or the nanoparticle or anisotropic nanoparticle comprising a polymeric matrix and at least one HIF inhibitor ranges in size from about 50 nanometers to about 5 microns. In some embodiments, the nanoparticle or anisotropic nanoparticle comprising at least one HIF inhibitor, or the nanoparticle or anisotropic nanoparticle comprising a polymeric matrix and at least one HIF inhibitor is at least 10, 20, 30, 40, or 50 nanometers in size. In some embodiments, the nanoparticle or anisotropic nanoparticle comprising at least one HIF inhibitor, or the nanoparticle or anisotropic nanoparticle comprising a polymeric matrix and at least one HIF inhibitor is less than 500, 400, 300, 200, 100, 50, or 5 microns in size. In some embodiments, the nanoparticle or anisotropic nanoparticle comprising at least one HIF inhibitor, or the nanoparticle or anisotropic nanoparticle comprising a polymeric matrix and at least one HIF inhibitor are small enough to have an enhanced permeability and retention (EPR) effect, such that they tend to accumulate in tumor tissue rather than normal tissue. For example, the nanoparticle or anisotropic nanoparticle comprising at least one HIF inhibitor, or the nanoparticle or anisotropic nanoparticle comprising a polymeric matrix and at least one HIF inhibitor can be less than 400 nanometers in size, such as between about 200 to about 225 nanometers in size, to take advantage of the EPR effect. In some embodiments, the nanoparticle or anisotropic nanoparticle comprising at least one HIF inhibitor, or the nanoparticle or anisotropic nanoparticle comprising a polymeric matrix and at least one HIF inhibitor are less than 200 nanometers in size. In some embodiments, the nanoparticle or anisotropic nanoparticle is biodegradable and/or biocompatible.

In some embodiments, the presently disclosed subject matter provides a method for inhibiting one or more hypoxia-inducible factors (HIFs) in a patient, the method comprising administering to a patient an anisotropic nanoparticle that is loaded with at least one HIF inhibitor, thereby inhibiting one or more HIFs in the patient. In some embodiments, the presently disclosed subject matter provides a method for inhibiting one or more hypoxia-inducible factors (HIFs) in a patient, the method comprising administering to a patient a nanoparticle comprising a polymeric matrix, wherein the nanoparticle is loaded with at least one HIF inhibitor, thereby inhibiting one or more HIFs in the patient. In some embodiments, the presently disclosed subject matter provides a method for inhibiting one or more hypoxia-inducible factors (HIFs) in a patient, the method comprising administering to a patient a nanoparticle comprising a poly (lactic acid)-based polymeric matrix, wherein the nanoparticle is loaded with at least one HIF inhibitor, thereby inhibiting one or more HIFs in the patient.

As used herein, the term "reduce" or "inhibit," and grammatical derivations thereof, refers to the ability of an agent to block, partially block, interfere, decrease, reduce or deactivate a biological molecule, pathway or mechanism of action. Thus, one of ordinary skill in the art would appreciate that the term "inhibit" encompasses a complete and/or partial loss of activity, e.g., a loss in activity by at least 10%, in some embodiments, a loss in activity by at least 20%, 30%, 50%, 75%, 95%, 98%, and up to and including 100%.

In some embodiments, the presently disclosed subject matter provides a method for treating a hypoxia-associated disease or disorder in a patient in need thereof, the method comprising administering to a patient an anisotropic nanoparticle that is loaded with at least one HIF inhibitor, thereby treating the hypoxia-associated disease or disorder in the patient. In some embodiments, the presently disclosed subject matter provides a method for treating a hypoxia-associated disease or disorder in a patient in need thereof, the method comprising administering to a patient a nanoparticle comprising a polymeric matrix, wherein the nanoparticle is loaded with at least one HIF inhibitor, thereby treating the hypoxia-associated disease or disorder in the patient. In some embodiments, the presently disclosed subject matter provides a method for treating a hypoxia-associated disease or disorder in a patient in need thereof, the method comprising administering to a patient a nanoparticle comprising a poly(lactic acid)-based polymeric matrix, wherein the nanoparticle is loaded with at least one HIF inhibitor, thereby treating the hypoxia-associated disease or disorder in the patient. In some embodiments, the nanoparticle comprising a polymeric matrix and at least one HIF inhibitor is anisotropic. In some embodiments, the nanoparticle comprising a poly(lactic acid)-based polymeric matrix and at least one HIF inhibitor is anisotropic. In some embodiments, the polymeric matrix is stretched before loading the HIF inhibitor to form an anisotropic nanoparticle comprising a polymeric matrix and at least one HIF inhibitor.

In some embodiments, the nanoparticle or anisotropic nanoparticle comprising a polymeric matrix and at least one HIF inhibitor further comprises at least one stimuli-sensitive nanoparticle. In some embodiments, the nanoparticle or anisotropic nanoparticle comprising a poly(lactic acid)-based polymeric matrix and at least one HIF inhibitor further comprises at least one stimuli-sensitive nanoparticle. In some embodiments, the presently disclosed method further comprises stimulating the at least one stimuli-sensitive nanoparticle in order to release the HIF inhibitor in a target location inside the patient, such as at the site of a solid tumor and/or at a metastatic site. In some embodiments, the presently disclosed method further comprises targeting the nanoparticle or the anisotropic nanoparticle to a target location inside the patient. In some embodiments, the surface of the nanoparticle or the anisotropic nanoparticle comprises at least one biomolecule, such as a targeting agent and/or a therapeutic agent. In some embodiments, the targeting and/or therapeutic agent is an antibody.

In some embodiments, stimulating the at least one stimuli-sensitive nanoparticle occurs by external stimulation of the patient. In some embodiments, the activation of the at least one stimuli-sensitive nanoparticle or the stimulation of the patient induces the shape of the anisotropic nanoparticle to change, such as from an anisotropic shape to another anisotropic shape or a generally spherical shape. In some embodiments, the change in shape of the anisotropic nanoparticle simultaneously happens with the release of at least one drug molecule from the anisotropic nanoparticle. In some embodiments, the release of at least one drug molecule occurs in a range from about 1 day to about two months after the anisotropic nanoparticle changes shape. In some embodiments, the change in shape of the anisotropic nanoparticle occurs in a patient. In some embodiments, the anisotropic nanoparticle is not taken up by a macrophage in the patient.

In some embodiments, the nanoparticle comprising a polymeric matrix and at least one HIF inhibitor is not anisotropic. It has been found herein that, in some embodiments, the presently disclosed formulations can be used for gradual release of HIF inhibitors without using anisotropic nanoparticles. In some embodiments, release of the HIF inhibitors occurs without application of an external stimulus.

In some embodiments, the hypoxia-associated disease or disorder is cancer. In some embodiments, the cancer is selected from the group consisting of brain, colon, breast, prostate, liver, kidney, lung, esophagus, head and neck, ovarian, cervical, stomach, colon, rectal, bladder, uterine, testicular, and pancreatic.

In some embodiments, the hypoxia-associated disease or disorder is an ocular disease. Non-limiting examples of ocular disease include diabetic retinopathy, macular degeneration, macular edema, glaucoma, lattice dystrophy, retinitis pigmentosa, age-related macular degeneration (AMD), photoreceptor degeneration associated with wet or dry AMD, other retinal degeneration, optic nerve drusen, optic neuropathy, and optic neuritis. In some embodiments, the ocular disease is selected from the group consisting of diabetic retinopathy, macular degeneration, and macular edema.

In some embodiments, the hypoxia-associated disease or disorder is chemotherapy resistance. As used herein, the term "chemotherapy resistance" refers to partial or complete resistance to chemotherapy drugs. In some embodiments, the presently disclosed methods further comprise administering to a patient a chemotherapeutic agent along with the HIF inhibitor. In some embodiments, the chemotherapeutic agent is loaded along with the HIF inhibitor into the presently disclosed nanoparticles. In some embodiments, the chemotherapeutic agent is given to the patient separately from the HIF inhibitor, such as by using a different administration route.

A "chemotherapeutic agent" is used to connote a compound or composition that is administered in the treatment of cancer. Chemotherapeutic agents include, but are not limited to, alkylating agents, such as thiotepa and cyclophosphamide; alkyl sulfonates, such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas, such as carmustine, chlorozotocin, fotemustine, lomustine, nimustine, ranimustine; antibiotics, such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs, such as ancitabine, azacitidine, 6-azauridine, carmofur, cytosine arabinoside, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenishers, such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g., paclitaxel and docetaxel; chlorambucil; gemcitabine; 6-thioguanine; mercaptopurine; platinum analogs, such as cisplatin and carboplatin; vinblastine; platinum; etoposide; ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylomithine; retinoic acid; esperamicins; capecitabine; and pharmaceutically acceptable salts, acids or derivatives of any of the above.

Chemotherapeutic agents also include anti-hormonal agents that act to regulate or inhibit hormone action on tumors, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, enzalutamide, leuprolide, abiraterone, and goserelin; and pharmaceutically acceptable salts, acids or derivatives of any of the above.

In some embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide, and irinotecan, as well as pharmaceutically acceptable salts, acids, or derivatives of any of these.

In some embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these.

In certain embodiments, the chemotherapeutic agent is an antimitotic agent, including, but not limited to, agents that bind tubulin. In some embodiments, the agent is a taxane. In certain embodiments, the agent is paclitaxel, cabazitaxel, or docetaxel, or a pharmaceutically acceptable salt, acid, or derivative of paclitaxel, cabazitaxel, or docetaxel. In certain alternative embodiments, the antimitotic agent comprises a vinca alkaloid, such as vincristine, binblastine, vinorelbine, or vindesine, or pharmaceutically acceptable salts, acids, or derivatives thereof.

In some embodiments, the chemotherapeutic agent is paclitaxel or gemcitabine.

The presently disclosed subject matter provides for the use of a composition comprising a nanoparticle comprising a polymeric matrix and at least one hypoxia-inducible factor (HIF) inhibitor for the treatment of a disease or disorder. The presently disclosed subject matter also provides for the use of a composition comprising a nanoparticle comprising a poly(lactic acid)-based polymeric matrix and at least one hypoxia-inducible factor (HIF) inhibitor for the treatment of a disease or disorder. In addition, the use of a composition comprising a nanoparticle comprising a polymeric matrix and at least one hypoxia-inducible factor (HIF) inhibitor for the manufacture of a medicament for the treatment of a disease or disorder is also provided. Further, the use of a composition comprising a nanoparticle comprising a poly(lactic acid)-based polymeric matrix and at least one hypoxia-inducible factor (HIF) inhibitor for the manufacture of a medicament for the treatment of a disease or disorder is also provided.

The terms "subject" and "patient" are used interchangeably herein. The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease.

Generally, the presently disclosed compositions (e.g., comprising an anisotropic shape memory particle comprising a polymeric matrix and at least one stimuli-sensitive nanoparticle or a nanoparticle comprising a polymeric matrix and at least one HIF inhibitor) can be administered to a subject for therapy by any suitable route of administration, including orally, nasally, transmucosally, ocularly, rectally, intravaginally, or parenterally, including intravenous, intramuscular, subcutaneous, intramedullary injections, as well as intrathecal, direct intraventricular, intravenous, intraarticular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

The phrases "systemic administration", "administered systemically", "peripheral administration" and "administered peripherally" as used herein mean the administration of compositions such that they enter the patient's system and, thus, are subject to metabolism and other like processes, for example, subcutaneous or intravenous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

The presently disclosed pharmaceutical compositions can be manufactured in a manner known in the art, e.g. by means of conventional mixing, dissolving, granulating, drageemaking, levitating, emulsifying, encapsulating, entrapping or lyophilizing processes.

In another embodiment, the presently disclosed pharmaceutical compositions may comprise PEGylated therapeutics (e.g., PEGylated antibodies). PEGylation is a well-established and validated approach for the modification of a range of antibodies, proteins, and peptides and involves the attachment of polyethylene glycol (PEG) at specific sites of the antibodies, proteins, and peptides (Chapman (2002) Adv. Drug Deliv. Rev. 54:531-545). Some effects of PEGylation include: (a) markedly improved circulating half-lives in vivo due to either evasion of renal clearance as a result of the polymer increasing the apparent size of the molecule to above the glomerular filtration limit, and/or through evasion of cellular clearance mechanisms; (b) improved pharmacokinetics; (c) improved solubility—PEG has been found to be soluble in many different solvents, ranging from water to many organic solvents such as toluene, methylene chloride, ethanol and acetone; (d) PEGylated antibody fragments can be concentrated to 200 mg/ml, and the ability to do so opens up formulation and dosing options such as subcutaneous administration of a high protein dose; this is in contrast to many other therapeutic antibodies which are typically administered intravenously; (e) enhanced proteolytic resistance of the conjugated protein (Cunningham-Rundles et. al. (1992) J. Immunol. Meth. 152:177-190); (0 improved bioavailability via reduced losses at subcutaneous injection sites; (g) reduced toxicity has been observed; for agents where toxicity is related to peak plasma level, a flatter pharmacokinetic profile achieved by subcutaneous administration of PEGylated protein is advantageous; proteins that elicit an immune response which has toxicity consequences may also benefit as a result of PEGylation; and (h) improved thermal and mechanical stability of the PEGylated molecule.

Pharmaceutical compositions for parenteral administration include aqueous solutions of compositions. For injection, the presently disclosed pharmaceutical compositions can be formulated in aqueous solutions, for example, in some embodiments, in physiologically compatible buffers, such as Hank's solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of compositions include fatty oils, such as sesame oil, or synthetic fatty acid esters, such as ethyl oleate or triglycerides, or liposomes. Optionally, the suspension also can contain suitable stabilizers or agents that increase the solubility of the compositions to allow for the preparation of highly concentrated solutions.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

Regardless of the route of administration selected, the presently disclosed compositions are formulated into pharmaceutically acceptable dosage forms such as described herein or by other conventional methods known to those of skill in the art.

In general, the "effective amount" or "therapeutically effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

The term "combination" is used in its broadest sense and means that a subject is administered at least two agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In some embodiments of the presently disclosed subject matter, the active agents are combined and administered in a single dosage form. In some embodiments, the active agents are administered in separate dosage forms (e.g., wherein it is desirable to vary the amount of one but not the other). The single dosage form may include additional active agents for the treatment of the disease state.

Further, the presently disclosed compositions can be administered alone or in combination with adjuvants that enhance stability of the agents, facilitate administration of pharmaceutical compositions containing them in certain embodiments, provide increased dissolution or dispersion, increase activity, provide adjuvant therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of two (or more) agents can be varied so long as the beneficial effects of the combination of these agents are achieved. Accordingly, the phrase "in combination with" refers to the administration of a presently disclosed composition and, optionally, additional agents either simultaneously, sequentially, or a combination thereof. Therefore, a subject administered a combination of a presently disclosed composition and, optionally, additional agents can receive a presently disclosed composition and, optionally, additional agents at the same time (i.e., simultaneously) or at different times (i.e., sequentially, in either order, on the same day or on different days), so long as the effect of the combination of all agents is achieved in the subject.

When administered sequentially, the agents can be administered within 1, 5, 10, 30, 60, 120, 180, 240 minutes or longer of one another. In other embodiments, agents administered sequentially, can be administered within 1, 2, 3, 4, 5, 10, 15, 20 or more days of one another. Where the agents are administered simultaneously, they can be administered to the subject as separate pharmaceutical compositions, each comprising either a presently disclosed composition and, optionally, additional agents, or they can be administered to a subject as a single pharmaceutical composition comprising all agents. In some embodiments, one agent is administered and the other agent is administered three days later. In some embodiments, one agent is administered and the other agent is administered 4, 5, 6, 7, 8, 9, 10, 15, 20 days or more later.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of an agent and at least one additional therapeutic agent is greater than the sum of the biological activities of the respective agents when administered individually.

Synergy can be expressed in terms of a "Synergy Index (SI)," which generally can be determined by the method described by F. C. Kull et al. Applied Microbiology 9, 538 (1961), from the ratio determined by:

$$Q_a Q_A + Q_b Q_B = \text{Synergy Index (SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

In another aspect, the presently disclosed subject matter provides a pharmaceutical composition and optionally, additional agents, alone or in combination with one or more additional therapeutic agents in admixture with a pharmaceutically acceptable excipient.

More particularly, the presently disclosed subject matter provides a pharmaceutical composition and, optionally, additional agents and a pharmaceutically acceptable carrier.

In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20$^{th}$ ed.) Lippincott, Williams and Wilkins (2000).

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

III. Kits Comprising the Presently Disclosed Particles

In general, a presently disclosed kit contains some or all of the components, reagents, supplies, and the like to practice a method according to the presently disclosed subject matter. In some embodiments, the term "kit" refers to any intended article of manufacture (e.g., a package or a container) comprising a presently disclosed nanoparticle or microparticle formulation.

In some embodiments, the kit comprises an anisotropic shape memory particle comprising a polymeric matrix and at least one stimuli-sensitive nanoparticle and a set of particular instructions for delivering a drug to a patient and/or treating a disease or disorder in a patient. In some embodiments, the kit comprises an anisotropic shape memory particle comprising a poly(lactic acid)-based polymeric matrix and at least one stimuli-sensitive nanoparticle and a set of particular instructions for delivering a drug to a patient and/or treating a disease or disorder in a patient.

In some embodiments, the kit comprises a nanoparticle comprising a polymeric matrix and at least one hypoxia-inducible factor (HIF) inhibitor and a set of particular instructions for inhibiting one or more HIFs and/or treating a hypoxia-associated disease or disorder. In some embodiments, the kit comprises a nanoparticle comprising a poly(lactic acid)-based polymeric matrix and at least one hypoxia-inducible factor (HIF) inhibitor and a set of particular instructions for inhibiting one or more HIFs and/or treating a hypoxia-associated disease or disorder.

The kit can be packaged in a divided or undivided container, such as a carton, bottle, ampule, tube, etc. The presently disclosed compositions can be packaged in dried, lyophilized, or liquid form. Additional components provided can include vehicles for reconstitution of dried components. Preferably all such vehicles are sterile and apyrogenic so that they are suitable for injection into a patient without causing adverse reactions.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Shape Memory Particles for Biomedical Uses

Materials and Methods

Hydrophobic Gold Nanoparticle Synthesis:

A modified version of Chatterjee et al. (2007) was used to synthesize hydrophobic gold nanoparticles. More specifically, lyophilized 1,2-Dioleoyl-sn-glycero-3-phosphocholine (Avanti® Polar Lipids; DOPC) was reconstituted at 25 mg/mL in chloroform and mixed with toluene, forming a 250 µg/mL solution (33 mL) which was vortexed for about 10 seconds. 5 mL of this solution put into 6 different 20 mL scintillation vials (underlying metal cap insert was extracted and discarded out of each cap to not reduce $Au^{3+}$. Tetrachloroauric acid trihydrate ($HAuCl_4$) was reconstituted in ultrapure distilled water to 100 mg/mL and served as a stock. 250 µL of the stock $HAuCl_4$ solution was mixed with 24.75 mL of ultra-pure distilled water forming a 1 mg/mL solution of $HAuCl_4$. 2 mL of this 1 mg/mL solution was added to each of the 6 20 mL scintillation vials already containing 5 mL of the 250 µg/mL DOPC solution in toluene. Each vial also contained a VWR magnetic stir bar. Prior to placing the scintillation vials on a multi-position stir plate, each vial was vortexed to produce a non-transparent, and to the extent possible, a homogenous mixture of the aqueous and organic phases prior to adding 1 mL of sodium citrate tribasic dihydrate at 10 mg/mL drop-wise. The stirring was continued for approximately 18 hours. Once completed, the organic and aqueous phases were allowed to sufficiently separate over a few minutes and the organic toluene phases were extracted, mixed, and placed into a new scintillation vial. All aqueous solvent was again taken out of the organic phase if phase separation occurred.

On the day we were to encapsulate the lipid-coated gold nanoparticles into the PDLLA microparticles, the gold nanoparticles (1 mL of gold nanoparticles in toluene in 1.5 mL tubes; total of 5 mL) were centrifuged at 16,000 rcf. All but the pellets were aspirated (975 µL) and replaced with an equal volume of dichloromethane (DCM). The gold nanoparticles were sonicated (Misonix) to become a homogenous mixture in the DCM. The 5 mL of gold nanoparticles in DCM were used directly in the single-emulsion encapsulation during PDLLA microparticle formation.

PDLLA Anisotropic Microparticle Synthesis and Characterization:

Two solutions of polyvinyl alcohol were made (PVA1=1% PVA; PVA0.5=0.5% PVA) in deionized MilliQ water. 200 mL of PVA0.5 were put into a beaker with a VWR stir bar spinning at 450 RPM). 100 mg of PDLLA were dissolved in the 5 mL of DCM containing gold nanoparticles and poured into 50 mL of PVA1 while being homogenized (5000 RPM). For fluorescent visualization of the particles, 1 mg of Nile Red or 7-amino-4-methyl coumarin was added to the DCM mixture. Then, the microparticle solution encapsulating gold nanoparticles was be poured into the already stirring PVA0.5 and stirred for an additional 4 hours to evaporate the organic solvent. Subsequently, the microparticles were washed 3× by centrifugation at 4° C. (4000 RPM; 5 minutes). After the $3^{rd}$ wash, the microparticles were resuspended in 1 mL of deionized water, triturated to avoid clumping, snap frozen in liquid nitrogen, lyophilized, and stored at a maximum temperature of 4° C. until further use. The particles were then deformed into anisotropic shapes by an automated thin film stretching procedure as described in Meyer et al. (2015).

To characterize the microparticle size and shape, scanning electron microscopy was utilized. Lyophilized particle samples were spread onto carbon tape mounted to aluminum tacks. The particles were then sputter coated with 30 nm of a gold-chromium alloy and imaged with a LeoFESEM. Size was determined by ImageJ analysis of the resulting SEM micrographs. Aspect ratio throughout all of the studies was determined through analysis of flat particles and taking the ratio of the longer axis to the shorter axis. For the fluorescent particle image analysis, confocal imaging was completed using a Zeiss 800 FCS confocal microscope.

Characterization of Gold Nanoparticles in PDLLA Microparticles:

In order to quantify the number of AuNPs within the microparticles, a standard curve was created; the AuNPs' stock concentration was assessed using Beer-Lambert's law (Liu et al., 2007) using an extinction coefficient of $3.189 \times 10^{10}$ $M^{-1}$ $cm^{-1}$. A standard curve was created using various dilutions of the AuNPs in toluene (1 mL) with 5 mg of pure PDLLA microparticles solvated in 400 µL of dimethyl sulfoxide (DMSO); 1 µL of the total volume of 1400 µL was used to assess the absorbance via NanoDrop (Thermo Scientific) (FIG. 3). When quantifying how many AuNPs there were per mg of particle, 5 mg of 4 unknown samples were solvated in 1 mL of toluene and 400 µL of DMSO. The number of AuNPs/µL of sample was interpolated with the standard curve and multiplied by 1400 (total volume in µL) and divided by 5 mg.

Laser Triggering of Shape Memory Effect:

For analysis of the temporal control of the shape memory effect, the particles were irradiated with a (laser specs) 532 nm laser at a power of 2 W distributed across a 5 mm diameter circular spot. The particles were irradiated at a concentration of $4*10^7$ particles/mL in a glass cuvette. Temperature was assessed with a Fluke thermocoupling device. After irradiation for the indicated period of time in the experiment, the particles were collected and imaged under SEM for evaluation of aspect ratio. The measured aspect ratio ($AR_m$) was then normalized to the initial aspect ratio ($AR_o$) to give percent shape reversion according to the following formula:

$$\frac{(AR_m - AR_o)}{1 - AR_o} * 100\%$$

Characterization of the spatial selectivity of the shape memory effect was achieved through immobilization of the particles in a PEG hydrogel at a concentration of $2*10^5$ particles/mL PEG gel. The hydrogel was then mounted to the laser and irradiated at a single circular spot approximately 5 mm in diameter for 5 minutes. Heating of PEG hydrogel was tracked by imaging with an FL-IR camera. After laser irradiation, the gel was imaged under confocal microscopy and individual images 200 µm in width were generated and stitched together for the length of the hydrogel. Aspect ratio was then quantified across the image to analyze the spatial dependence of the shape memory effect on the laser spot size.

Cell Uptake Experiments:

Cell uptake of the particles triggered to undergo the shape memory effect was analyzed using RAW 264.7 macrophages. Cell uptake was evaluated using flow cytometry and confocal microscopy. For flow cytometry, the cells were seeded onto a 96-well plate at a density of 30,000 cells/well two days prior to the start of the experiment. On the day of the experiment, the media was aspirated, and media containing the particles at the indicated dose was added. The cells were then incubated for 4 hours at 37° C. and at the end of 4 hours, they were washed 3 times with 1×PBS. For distinction of particles from cells, the cells were then stained with carboxyfluorescein succinyl ester (CFSE) according to the manufacturer's protocol. CFSE stained cells were then removed from the plate with vigorous trituration and were analyzed by flow cytometry. For confocal microscopy, the cells were cultured on a LabTek chamber slide at a density of 30,000 cells per well. After 4 hours incubation time with the particles, the excess particles were washed away with 3 washes of 1×PBS and then the cells were fixed with 10% formalin for 15 minutes at room temperature. Following fixation and washing, the cells were stained with Alexa 647 phalloidin for actin visualization and DAPI for nuclear visualization following the manufacturer's protocols. The cells were then imaged using a Zeiss FCS 800 confocal microscope. Cell viability was evaluated using a cell titer assay following the manufacturer's protocol.

Results

Shape memory microparticles were created that were composed of poly (D,L lactic acid) (PDLLA) matrix encapsulating gold nanoparticles (FIG. 1A). A representative shape memory activation mechanism is shown in FIG. 1B. A temporary stretched shape of spherical gold nanoparticles-embedded PDLLA microparticles was obtained using film-stretching at comparably low temperature without interrupting polymeric physical entanglement networks in the microparticles (FIG. 1B).

FIG. 2A, FIG. 2B, FIG. 2C, and FIG. 2D show the shape memory effect of polymeric microparticles. Poly (D,L lactic acid) microparticles (FIG. 2A) were stretched either at 65° C. (FIG. 2B) or 90° C. (FIG. 2C) to an anistropic shape, incubated for 1 min, 5 min, 15 min, 30 min, or 60 min and then analyzed under SEM. Image analysis demonstrated that the shape memory effect triggered at low temperature stretched particles, but not at high temperature stretched particles. FIG. 2D shows that polymer alignment was present to a higher degree in 65° C. stretched particles as opposed to 90° C. stretched particles, indicating polymer physical crosslinks as the driving force behind the observed shape memory effect.

The shape memory microparticle morphology was examined after stretching and demonstrated the anisotropic shape of the stretched microparticles (FIG. 3A, FIG. 3B, FIG. 3C, FIG. 3D, and FIG. 3E). Spherical (FIG. 3A) and non-spherical (FIG. 3B) particles were characterized using SEM. FIG. 3C shows size characterization of the spherical particles demonstrating a size of about 4 µm. FIG. 3D and FIG. 3E show absorbance spectrum (FIG. 3D) and standard curve (FIG. 3E) of AuNPs in the presence of pure PDLLA microparticles.

Figure 4A:
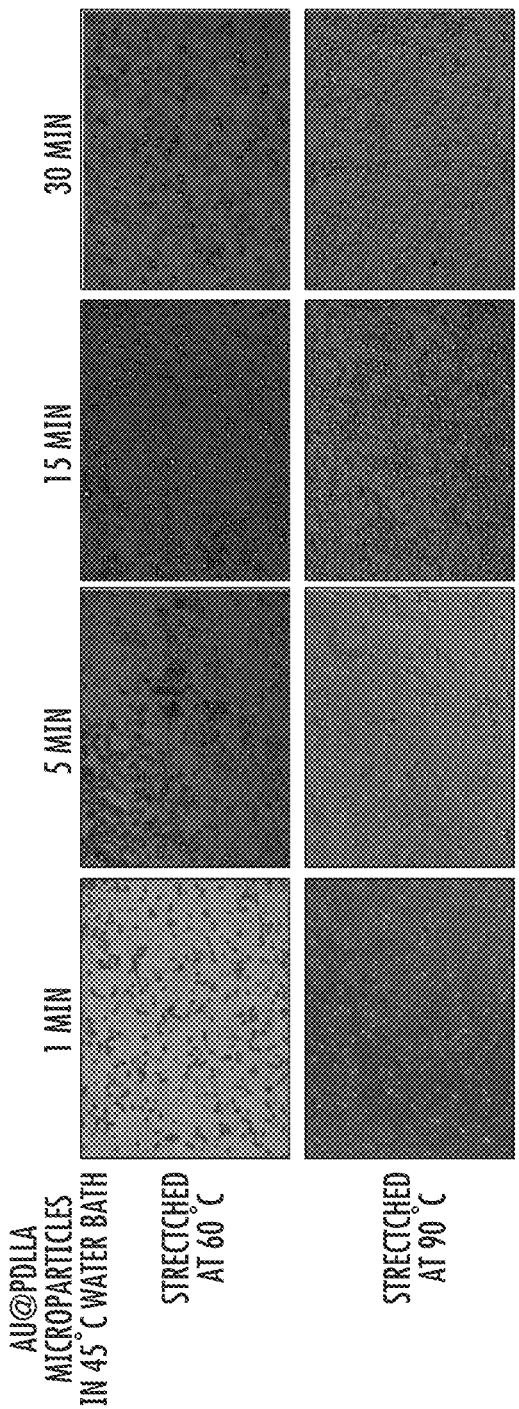
Figure 4D:
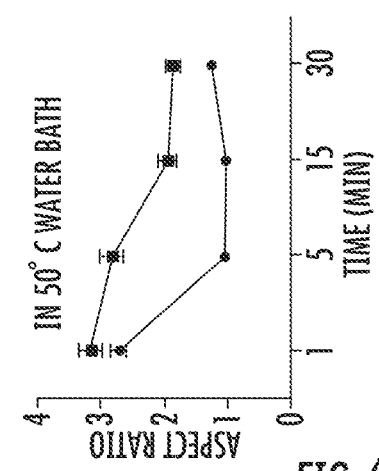
Figure 4C:
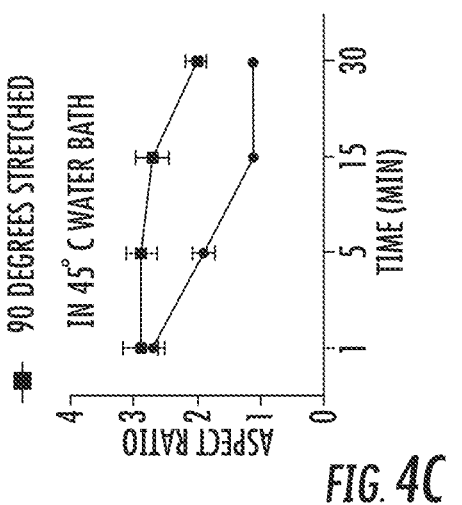
Figure 4B:
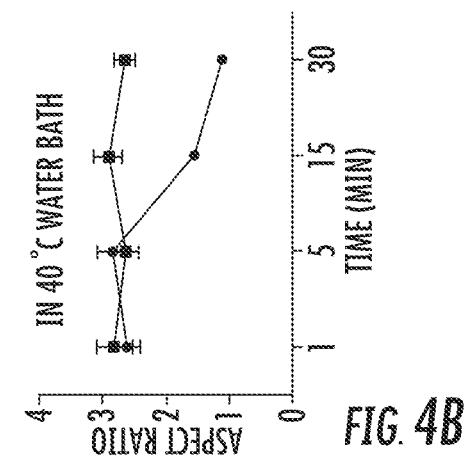

The shape memory effect of microparticles was confirmed by bulk heating of the polymeric particles (FIG. 4A to FIG. 4D). Optical microscopy images showed that in the 45° C. water bath, the particles stretched at 60° C. gradually changed their anisotropic shape to spherical shape within 30 min, while the particles stretched at 90° C. maintained their anisotropic shape up to 30 min. Quantitative analyses, as shown in FIG. 4B to FIG. 4D, demonstrated that the aspect ratios of particles stretched at 60° C. quickly dropped down in all three water baths, and took 30 min, 15 min, and 5 min to decrease to 1 at 40° C., 45° C., and 50° C., respectively. In contrast, the aspect ratio of the particles stretched at 90° C. maintained around 3 in 40° C. water bath, but only slightly decreased to around 2 in higher temperature water baths.

The shape memory effect of microparticles encapsulating gold nanoparticles was also achieved by laser trigger (FIG. 5A, FIG. 5B, FIG. 5C, FIG. 5D, FIG. 5E, FIG. 5F, FIG. 5G, and FIG. 5H). Particles were stretched at 65° C. (FIG. 5A) or 90° C. (FIG. 5B) and lasered for 0 min, 1 min, 2 min, 3 min, or 5 min. The aspect ratio of shape memory microparticles stretched at 60° C. quickly decreased within 5 min laser exposure at 3.8 W (FIG. 5C). In contrast, PDLLA microparticles stretched at 90° C. maintained their anisotropic shape (FIG. 5C). This indicates that the microparticles lost their shape-memory effect due to reorganization of the polymeric entanglement network during the stretching process at 90° C. Importantly, the maximum temperature measured during laser trigger was 42° C., which is within human body-friendly temperature range. FIG. 5D shows that the particles stretched at 65° C. achieved 100% aspect ratio reversion and the particles at 90° C. achieved 20% aspect ratio reversion. The temperature of the samples did not differ over the course of heating (FIG. 5E). In addition, the particles immobilized in a PEG hydrogel demonstrated spatial selection of the shape memory effect. The area where the laser was applied was the area where particles achieved shape memory (FIG. 5F). Thermal IR imaging of the PEG hydrogel demonstrated heating throughout the entire gel (FIG. 5G). The aspect ratio analysis of stitched confocal images demonstrated near complete reversion of particles only at the spot where the laser irradiated the particles (FIG. 5H).

Laser triggering of shape memory particles was found to have an effect on cellular phagocytosis of microparticles through shape uptake effects. FIG. 6A and FIG. 6B show confocal images of macrophages uptaking spherical particles (FIG. 5A) and stretched particles (FIG. 6B). These images demonstrate macrophage phagocytic preference for laser irradiated, shape retracted particles over ellipsoidal particles (FIG. 6A and FIG. 6B). The percentage uptake was calculated for the spherical particles and the ellipsoid particles and is shown in graphic form in FIG. 6C.

FIG. 7A, FIG. 7B, and FIG. 7C show that phagocytic cells demonstrate different responses to differentially stretched particles that are triggered by the laser. Confocal imaging demonstrated that there is a preference of macrophages to phagocytically take up spherical particles in high quantities compared to non-spherical particles.

FIG. 8A, FIG. 8B, FIG. 8C, and FIG. 8D show spherical (FIG. 8A) and non-spherical (FIG. 8B) PDLLA microparticles encapsulating gold nanoparticles imaged under TEM to analyze the presence of gold nanoparticles. Zoomed in pictures of the edges (area of minimal polymer TEM image interference) of spherical (FIG. 8C) and stretched (FIG. 8D) microparticles demonstrated the presence of gold nanoparticles (red arrows) encapsulated within the polymeric microparticle.

FIG. 9 shows a representative mixed particle shape memory experiment in which particles stretched at 65° C. (blue) and particles stretched at 90° C. were mixed in a 1:1 ratio and heated at 40° C. for the indicated time. Confocal imaging of the subsequent samples demonstrates a sole dependence of the shape memory effect on the particle stretching temperature.

FIG. 10 shows cell viability was not altered by exposure of the cell to various doses. Cell metabolic rate was assessed after 4 hr. of exposure to the particles by using an MTS assay. The rates were then normalized to untreated cells to give percent metabolic activity. No significant reduction was noted.

SUMMARY

It is believed that this is the first disclosure of the fabrication of biocompatible shape memory microparticles that can be induced in a human physiological environment. Biocompatible light-induced shape memory microparticles composed of PDLLA matrix encapsulating gold nanoparticles (Au@PDLLA microparticles) have been successfully developed.

Either heat or laser light could be applied to trigger the shape memory effect of the gold nanoparticles-embedded PDLLA microparticles. These shape memory microparticles underwent a shape change from a temporary stretched shape to an original spherical shape due to stress recovery while maintaining the polymeric entanglement network. Such a shape memory effect is universal to all polymers, opening a new window to exploring new shape-memory materials for bioapplications.

In some embodiments, these materials are especially useful to actively control cellular uptake and/or drug delivery for tissue regeneration or tumor therapy through a direct or indirect trigger.

Example 2

Polymeric Nanoparticles Containing Inhibitors of Hypoxia-Inducible Factors (HIFs) Methods Nanoparticle Precipitation:

All drug formulations were formed using a single-emulsion nanoprecipitation method. More specifically, the poly (D,L-lactide-co-glycolide) (PLGA)-acriflavine nanoparticle formulation was formed as follows: A 5 mg/mL solution of acriflavine in methanol was mixed with a 33.3 mg/mL solution of commercially obtained poly(D,L-lactide-co-glycolide) (PLGA) (Resomer® 50:50; Molecular weight: 7 kDa-17 kDa) in acetone in a 1:4 volume to volume ratio. This acriflavine/PLGA mixture was then injected into a 10 mg/mL bovine serum albumin (BSA) solution in ultra pure distilled water in a 1:2.5 volume to volume ratio and immediately sonicated using a Misonix sonicator at an amplitude of 60 for 2 minutes. The organic phase was allowed to evaporate in a vacuum chamber on ice for 24 hours. The formulation was then washed three times via ultracentrifugation at 39000 RCF for 15 minutes and subsequently frozen and lyophilized.

The PLGA-doxorubicin formulation was formed similarly to the acriflavine formulation but using a 1.25 mg/mL solution, rather than a 5 mg/mL solution, in methanol. The PLGA-digoxin formulation was made similarly as well but using a 5 mg/mL solution in a 50:50 mixture of dichloromethane (methylene chloride) and methanol.

Diameter and Zeta Potential:

The diameter of each of the formulations was quantified using nanoparticle tracking analysis software (NanoSight) in phosphate buffered saline. The zeta potential was quantified using a Malvern Zetasizer in water.

Drug Loading and Release Quantification:

The drug loading and release was quantified using fluorescence for acriflavine (excitation and emission of 430 and 515 nm, respectively) and doxorubicin (excitation and emission of 485 and 590 nm, respectively). The drug loading and release for the PLGA-digoxin formulation was quantified using a digoxin ELISA kit (Monobind).

The release was accomplished at 37° C. in phosphate buffered saline. The samples at various times were centrifuged and the supernatant was frozen, lyophilized, and re-constituted in either dimethyl sulfoxide (DMSO) for acriflavine and doxorubicin or in 70% ethanol for digoxin. The original concentration of the PLGA-drug formulations to assess the release in time for acriflavine and doxorubicin were 1 mg/mL and for digoxin was 20 mg/mL.

The loading was quantified for the PLGA-acriflavine and PLGA-doxorubicin formulations by dissolving the samples in acetone, evaporating in a vacuum chamber and then re-constituting in DMSO. These samples were centrifuged to separate the PLGA prior to quantification. The loading for the PLGA-digoxin was quantified by adding 1 M HCl and 1 M NaOH, neutralizing the pH, freezing, lyophilizing, and then re-constituting in 70% ethanol.

Statistics:

All errors reported are standard errors of the mean.

Results

Diameter and Zeta Potential:

The diameter of the PLGA-acriflavine, PLGA-doxorubicin and PLGA-digoxin formulations were 220±20 (n=2), 210±10 (n=2), and 210±10 nm (n=3), respectively (FIG. 11). The zeta potentials of the PLGA-acriflavine, PLGA-doxorubicin and PLGA-digoxin formulations were −13.9±0.7 (n=3), −13.0±0.9 (n=3), and −15.2±0.1 mV (n=3), respectively (FIG. 11).

Drug Loading and Release Quantification:

The loading for the PLGA-acriflavine, PLGA-doxorubicin and PLGA-digoxin formulations were 43±3, 15.0±0.5, and 90±10 µg/mg, respectively, of the encapsulated PLGA-drug mass. The cumulative release for the PLGA-acriflavine, PLGA-doxorubicin and PLGA-digoxin formulations reached 15.1±0.8 (FIG. 12), 7.5±0.8 (FIG. 14), and 53±4 µg/mg (FIG. 12), respectively, of PLGA-drug. The percent releases peaked for acriflavine, doxorubicin and digoxin at 35±2 (FIG. 13), 50±5 (FIG. 13), and 56±4% (FIG. 15), respectively. The majority of the drug from the PLGA-acriflavine and PLGA-doxorubicin formulations was released over approximately 1 week (FIG. 12 and FIG. 13), whereas the PLGA-digoxin formulation released the drug over a much longer duration on the order of several months (FIG. 14 and FIG. 15).

Temperature Dependence of Drug Release:

Paclitaxel release from the PLA-based polymers exhibited strong dependence on the difference between drug release temperature and polymer Tg (FIG. 16A). FIG. 16B shows that similar results were also found in doxorubicin release from microparticles. FIG. 16C shows that digoxin release demonstrated similar release kinetics even from nanoparticles with much smaller sizes (as seen in FIG. 11).

Digoxin Blocks Paclitaxel-Induced BCSC Enrichment in TNBC Orthografts:

The combination of paclitaxel and digoxin had a significantly greater inhibitory effect on tumor growth compared with either digoxin or paclitaxel alone (FIG. 17A). The freshly harvested tumors were dissociated into single cell suspensions and subjected to the Aldefluor assay, which revealed that compared with saline treatment, paclitaxel significantly increased the percentage of aldehyde dehydrogenase-expressing (ALDH$^+$) cells, which are enriched for breast cancer stem cells (FIG. 17B). In contrast, digoxin significantly decreased the percentage of ALDH$^+$ cells and abrogated the paclitaxel-induced enrichment of ALDH$^+$ cells (FIG. 17B). In the same tumors, paclitaxel increased the expression of IL-6, IL-8, and MDR1 mRNA, which promote the breast cancer stem cell phenotype, and this effect was inhibited by digoxin (FIG. 17C).

Coadministration of Digoxin with Gemcitabine Prevents Tumor Relapse:

To examine the effect of HIF inhibition on tumor relapse, MDA-MB-231 cells were implanted into the mammary fat pad of Scid mice. When the tumor became palpable, the mice were randomized to receive intraperitoneal injections of saline, gemcitabine (20 mg/kg on days 5, 10, 15, 20, and 25), or the combination of digoxin (2 mg/kg on days 1-25) and gemcitabine. Treatment was stopped when tumors were no longer palpable in the mice receiving digoxin/gemcitabine combination therapy. Although treatment with gemcitabine markedly reduced tumor growth, after treatment was discontinued, rapid tumor growth resumed (FIG. 18). In contrast, gemcitabine/digoxin combination therapy not only eliminated the primary tumor but also prevented any immediate tumor relapse.

SUMMARY

It has been found that the expression of hypoxia-inducible factors (HIFs) is a hallmark of intratumoral hypoxia that is associated with chemotherapy resistance. It has been demonstrated that coadministration of a HIF inhibitor, such as digoxin, with cytotoxic chemotherapy, such as paclitaxel or gemcitabine, overcame the resistance of breast cancer stem cells to chemotherapy, leading to tumor eradication in mice. These experiments demonstrate the utility of digoxin in blocking the counter-therapeutic effect of cytotoxic chemotherapy on breast cancer stem cells, thereby preventing tumor recurrence following therapy. Increased toxicity of digoxin in humans prevents use of the free drug in this manner, but this obstacle can be overcome by use of polymeric shape memory nanoparticles containing HIF inhibitors, which are not released until the particles have localized within the tumor.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Chatterjee et al., Synthesis and Self-assembly of DMPC-conjugated Gold Nanoparticles. *MRS Proceedings* 2007, 1061, 1061-MM09-08 doi:10.1557/PROC-1061-MM09-08.

Liu et al., Extinction coefficient of gold nanoparticles with different sizes and different capping ligands. *Colloids Surf B*, 58 (2007), pp. 3-7.

Meyer et al., An automated multidimensional thin film stretching device for the generation of anisotropic polymeric micro- and nanoparticles. *J. Biomed. Mater. Res. A.* 2015, 103(8):2747-57.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A composition consisting of an anisotropic shape memory particle comprising at least one stimuli-sensitive nanoparticle encapsulated in a polymer matrix.

2. The composition of claim 1, wherein a surface of the anisotropic shape memory particle comprises at least one targeting agent and/or at least one therapeutic agent.

3. The composition of claim 2, wherein the at least one targeting agent and/or the at least one therapeutic agent is selected from the group consisting of a small molecule, carbohydrate, sugar, protein, peptide, nucleic acid, antibody or antibody fragment thereof, hormone, hormone receptor, receptor ligand, and cancer cell specific ligand.

4. The composition of claim 1, wherein the polymer matrix comprises poly(D,L-lactide-co-glycolide) (PLGA) or poly (D,L-lactic acid) (PDLLA).

5. The composition of claim 1, wherein the anisotropic shape memory particle ranges in size from about 10 nanometers to about 500 microns.

6. The composition of claim 1, wherein the at least one stimuli-sensitive nanoparticle comprises gold and/or iron.

7. The composition of claim 2, wherein the at least one therapeutic agent is a hypoxia-inducible factor (HIF)inhibitor.

8. The composition of claim 1, further comprising a chemotherapeutic agent.

9. The composition of claim 8, wherein the chemotherapeutic agent is paclitaxel or gemcitabine.

10. The composition of claim 7, wherein the HIF inhibitor is selected from the group consisting of a hypoxia-inducible factor-1 (HIF-1) inhibitor, a hypoxia-inducible factor-2 (HIF-2) inhibitor, and a hypoxia-inducible factor-3 (HIF-3) inhibitor.

* * * * *